(12) United States Patent
Bhat et al.

(10) Patent No.: US 7,799,970 B2
(45) Date of Patent: Sep. 21, 2010

(54) PLANT REGULATORY SEQUENCES FOR SELECTIVE CONTROL OF GENE EXPRESSION

(75) Inventors: Deepti G. Bhat, San Diego, CA (US); Molian Deng, Grover, MO (US); Robert J. Eilers, St. Louis, MO (US); Donald E. Nelson, Stonington, CT (US); Daniel J. Tennessen, St. Louis, MO (US)

(73) Assignee: Monsanto Technology LLC, St. Louis, MO (US)

( * ) Notice: Subject to any disclaimer, the term of this patent is extended or adjusted under 35 U.S.C. 154(b) by 1584 days.

(21) Appl. No.: 10/545,472

(22) PCT Filed: Feb. 13, 2004

(86) PCT No.: PCT/US2004/004499

§ 371 (c)(1),
(2), (4) Date: Aug. 12, 2005

(87) PCT Pub. No.: WO2004/074442

PCT Pub. Date: Sep. 2, 2004

(65) Prior Publication Data

US 2006/0212970 A1 Sep. 21, 2006

Related U.S. Application Data

(60) Provisional application No. 60/447,833, filed on Feb. 14, 2003.

(51) Int. Cl.
*C12N 15/29* (2006.01)
*C12N 15/82* (2006.01)
*A01H 5/00* (2006.01)
*A01H 5/10* (2006.01)

(52) U.S. Cl. ............ 800/278; 536/24.1; 800/298; 800/320.1; 800/312

(58) Field of Classification Search ............ None
See application file for complete search history.

(56) References Cited

U.S. PATENT DOCUMENTS 6,337,430 B1 * 1/2002 Ishige et al. ............ 800/278
7,196,245 B2 * 3/2007 Jiang et al. ............ 800/278
2008/0034453 A1 * 2/2008 Cheikh et al. ............ 800/294

OTHER PUBLICATIONS

Kagaya et al (1995, Mol. Gen. Genet. 248 :668-674).*
Lin et al (2008, Journal of Experimental Botany 59(15):4271-4287).*
Benfey et al., "The CaMV 35S enhancer contains at least two domains which can confer different developmental and tissue-specific expression patterns," *EMBO J.*, 8(8):2195-2202, 1989.
Cho et al., "Regulation of root hair initiation and expansin gene expression in arabidopsis," *The Plant Cell*, 14:3237-3253, 2002.
Clements et al., "Characterization of a non-abscission mutant in lupinus angustifolius. I. Genetic and structural aspects," *Amer. J. Of Bot.*, 88(1):31-42, 2001.
European Union Chromosome 3 *Arabidopsis* Sequencing Consortium, "Sequence and analysis of chromosome 3 of the plant *Arabidopsis thaliana*," *Nature*, 408:820-822, 2000.
GenBank Accession No. AAC63630.1, dated Mar. 11, 2002.
GenBank Accession No. CAA78909.1, dated Apr. 18, 2005.
Kim et al., "A 20 nucleotide upstream element is essential for the nopaline synthase (nos) promoter activity," *Plant Molecular Biology*, 24:105-117, 1994.
Mandel et al., "Molecular characterization of the *Arabidopsis* floral homeotic gene APETALA1," *Nature*, 360:273-277, 1992.
Odell et al., "Identification of DNA sequences required for activity of the cauliflower mosaic virus 35S promoter," *Nature*, 313:810-812, 1985.
Piechulla et al., "Identification of tomato Lhc promoter regions necessary for circadian expression," *Plant Molecular Biology*, 38:655-662, 1998.
Taylor et al., "Tansley review No. 127—Signals in abscission," *New Phytologist*, 151:323-339, 2001.
Welsch et al., "Structural and functional characterization of the phytoene synthase promoter from *Arabidopsis thaliana*," *Planta*, 216:523-534, 2003.

* cited by examiner

*Primary Examiner*—Stuart F. Baum
(74) *Attorney, Agent, or Firm*—Erin C. Robert, Esq.; Sonnenschein Nath & Rosenthal LLP

(57) ABSTRACT

The current invention relates to enhancing gene expression in plants. A promoter drives the expression of structural genes or other polynucleotides in the abscission zone of a plant is provided. The sequence of such a promoter, and its use in a transgenic plant comprising such a promoter, is described.

30 Claims, 18 Drawing Sheets

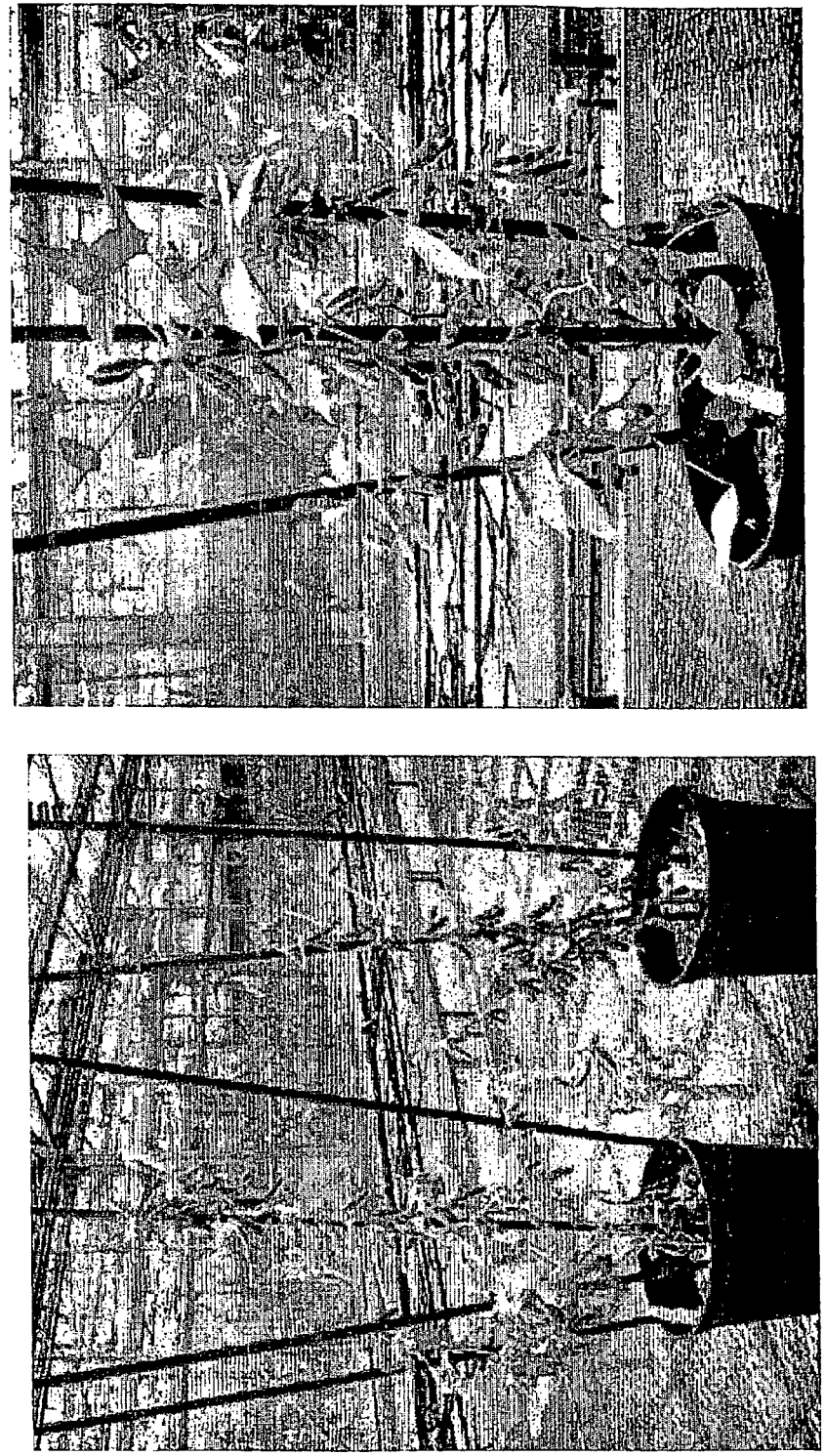
Figure 10. pMON73967 (Event GM_A32054) Transgenic Plant Greenhouse Characterization

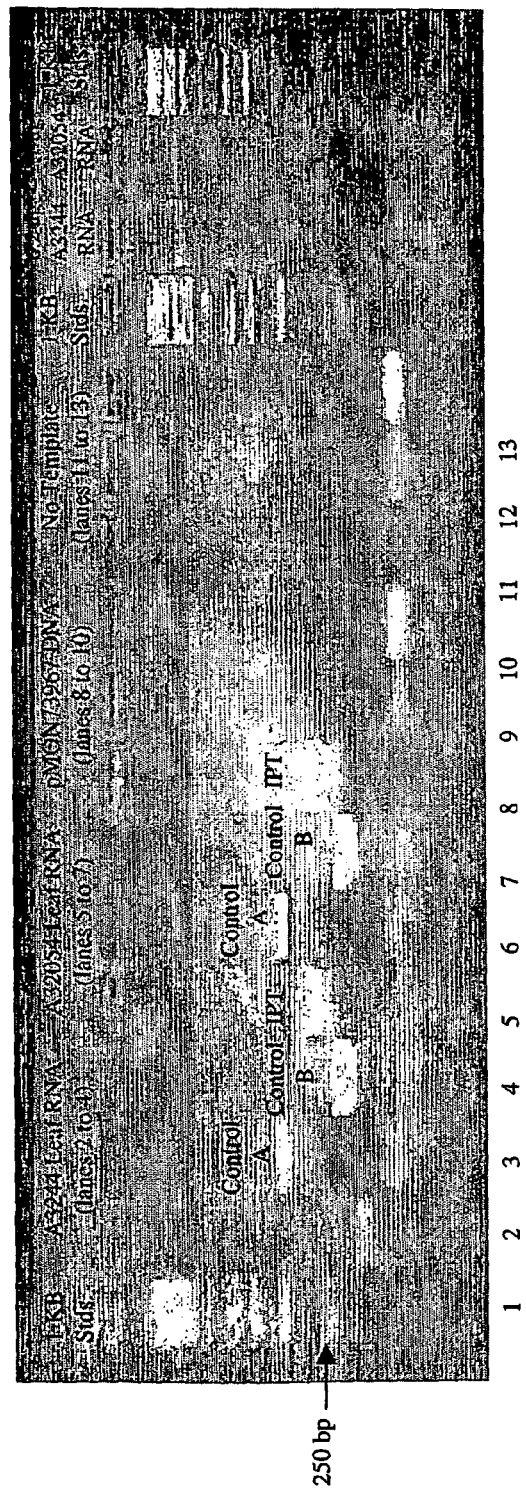
Figure 11. Characterization pMON73967 Transgenic Plant, Event GM_A32054, selection 64 RT-PCR Analysis
Note: 2% Agarose gel. Loaded 2 ug RNA per RT-PCR reaction.

Figure 12. pMON73967 Transgenic Event GM_A32054 Segregating Population Greenhouse Results

| Pedigree | | Total Pods/Main Stem | Total Pods on Branches | Total Pods | Total Branches | Total Nodes / Main Stem | Total Nodes All Branches | Total Nodes | Total # Seeds | Grams of Seed per Plant | Seed Weight in MG |
|---|---|---|---|---|---|---|---|---|---|---|---|
| GM_A32054:@: n = 102 | Median | 50 | 93 | 144 | 5 | 24 | 60 | 85 | 284 | 45 | 154 |
| GM_A32054:@: n = 102 | Mean | 48 | 86 | 133 | 6 | 22 | 61 | 84 | 282 | 44 | 153 |
| A3244 | n = 50 Median | 38 | 24 | 61 | 3 | 17 | 15 | 32 | 160 | 31 | 194 |
| A3244 | n = 50 Mean | 36 | 27 | 63 | 3 | 17 | 16 | 33 | 156 | 30 | 188 |
| Note: Only included plants which set seed and some plants had delayed maturity. | | | | | | | | | | | |

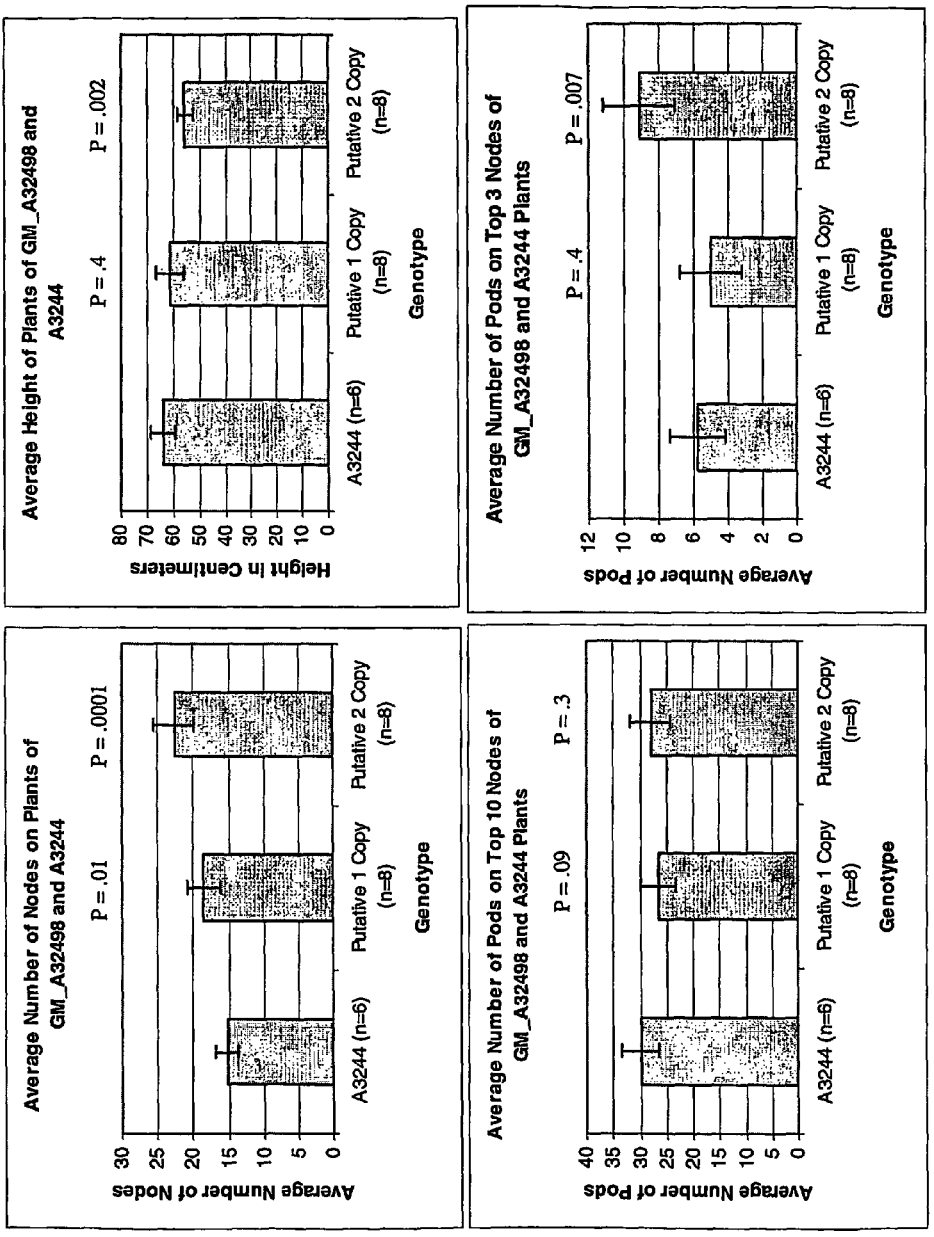
Figure 13. Effect of pMON73967 on Node Number and Plant Height in Field Grown Line Advancement

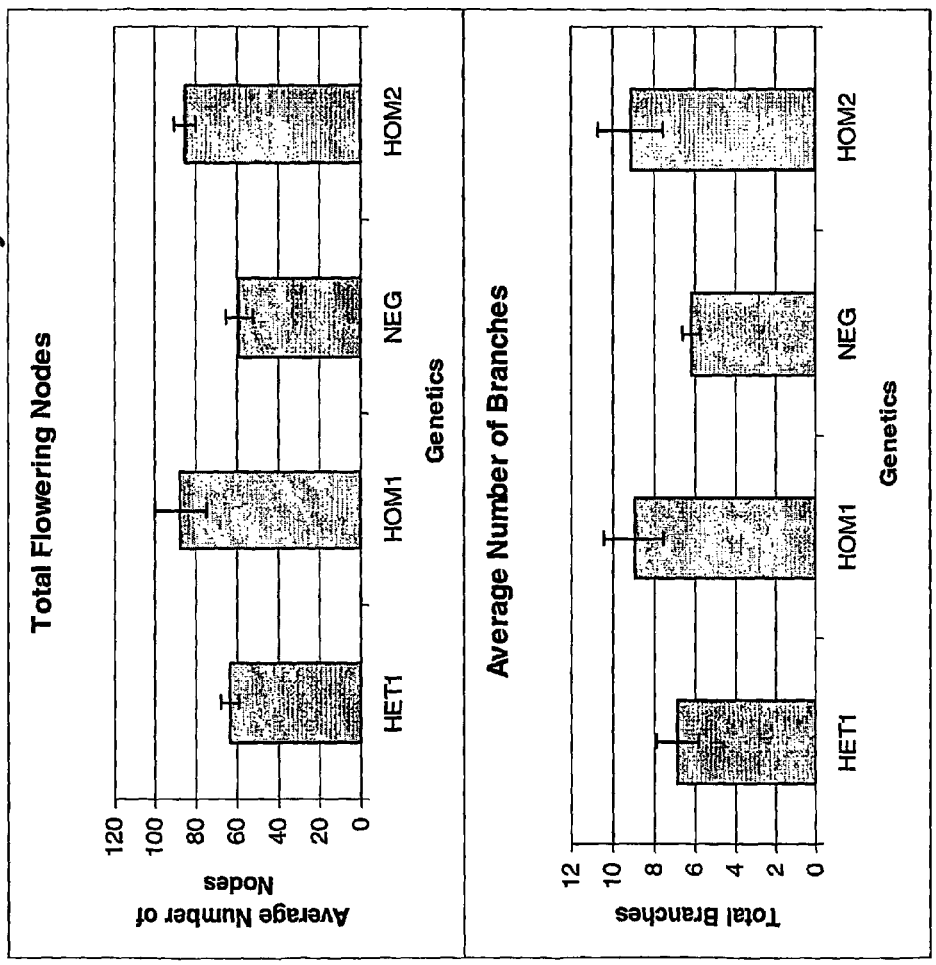
Figure 14. Effect of pMON73967 (Event GM_A32498) on Node Number and Branching in Growth Chamber Study

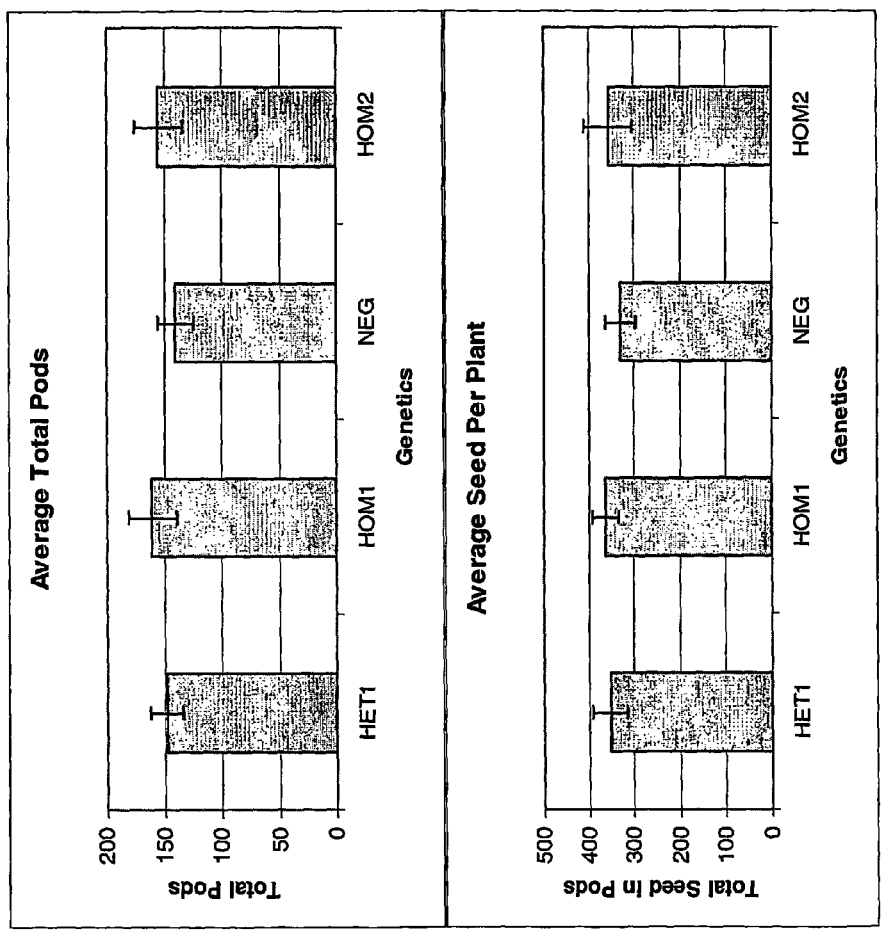
Figure 15. Effect of pMON73967 (Event GM_A32498) on Pod Set and Seed Production in Growth Chamber Study Figure 16. Effect of pMON73967 (Event GM_A32498) on Phenotype in Growth Chamber Study

| Pedigree | Genetics | Statistic | Total Nodes | Total pods | Total Seed | Total Branches | Flowering Onset | Maturity |
|---|---|---|---|---|---|---|---|---|
| GM_A32498:@.0105. | HET1 | Average | 63 | 148 | 353 | 7 | Normal | Normal |
| GM_A32498:@.0105. | HET1 | Std. Dev. | 4.4 | 14.3 | 37.1 | 1.1 | Normal | Normal |
| GM_A32498:@.0105. | HET1 | % NEG | 108 | 106 | 107 | 111 | Normal | Normal |
| GM_A32498:@.0105. | HET1 | Median | 64 | 149 | 361 | 7 | Normal | Normal |
| GM_A32498:@.0105. | HET1 | T Test | 0.17322 | 0.36854 | 0.30381 | 0.22859 | Normal | Normal |
| GM_A32498:@.0105. | HOM1 | Average | 88 | 160 | 363 | 9 | Normal | Slight Delay |
| GM_A32498:@.0105. | HOM1 | Std. Dev. | 12.7 | 20.6 | 28.7 | 1.4 | Normal | Slight Delay |
| GM_A32498:@.0105. | HOM1 | % NEG | 149 | 114 | 110 | 145 | Normal | Slight Delay |
| GM_A32498:@.0105. | HOM1 | Median | 85 | 150 | 353 | 9 | Normal | Slight Delay |
| GM_A32498:@.0105. | HOM1 | T Test | 0.00205 | 0.11729 | 0.14040 | 0.00291 | Normal | Slight Delay |
| GM_A32498:@.0105. | NEG | Average | 59 | 140 | 331 | 6 | Normal | Normal |
| GM_A32498:@.0105. | NEG | Std. Dev. | 6.6 | 15.5 | 33.0 | 0.4 | Normal | Normal |
| GM_A32498:@.0105. | NEG | % NEG | 100 | 100 | 100 | 100 | Normal | Normal |
| GM_A32498:@.0105. | NEG | Median | 59 | 149 | 351 | 6 | Normal | Normal |
| GM_A32498:@.0050. | HOM2 | Average | 85 | 155 | 357 | 9 | Normal | Slight Delay |
| GM_A32498:@.0050. | HOM2 | Std. Dev. | 5.0 | 20.8 | 54.0 | 1.6 | Normal | Slight Delay |
| GM_A32498:@.0050. | HOM2 | % NEG | 145 | 111 | 108 | 147 | Normal | Slight Delay |
| GM_A32498:@.0050. | HOM2 | Median | 87 | 155 | 355 | 9 | Normal | Slight Delay |
| GM_A32498:@.0050. | HOM2 | T Test | 0.00001 | 0.20857 | 0.36508 | 0.00245 | Normal | Slight Delay |

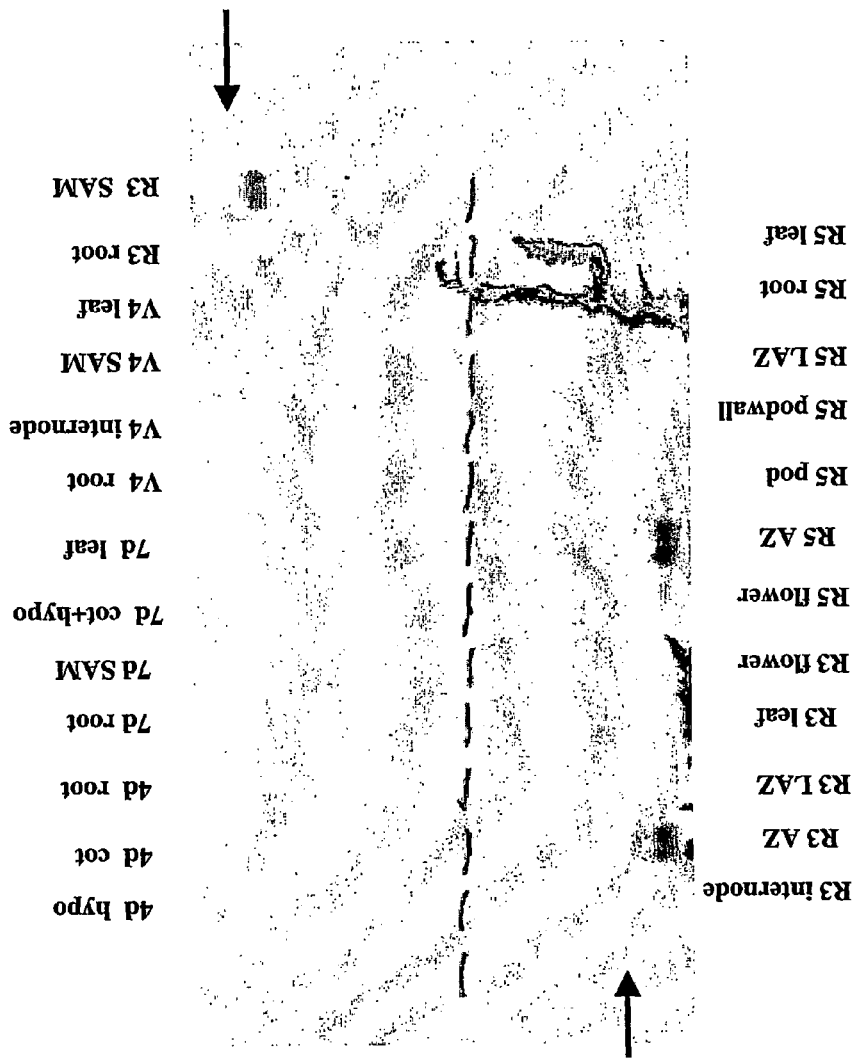
Figure 17. Expression of Endogenous A6 on a Developmental Northern Showing Expression in Soybean.

PLANT REGULATORY SEQUENCES FOR SELECTIVE CONTROL OF GENE EXPRESSION

CROSS REFERENCE TO RELATED APPLICATIONS

This application is the U.S. National Stage of International (PCT) Application No. PCT/US2004/004499, filed on Feb. 13, 2004, which claims the benefit under 35 USC §119(e) of the United States Code to provisional application Ser. No. 60/447,833 filed on Feb. 14, 2003, herein incorporated by reference.

INCORPORATION OF SEQUENCE LISTING

A copy of the sequence listing (18 sheets) and a computer readable form (CRF) of the sequence listing in the form of the electronic file named "38-21_52732C.txt" (with a file size of 32 kilobytes measured in the MS-WINDOWS® operating system, and which was created on 17 Nov. 2008) are herein incorporated by reference.

FIELD OF THE INVENTION

The present invention relates to the isolation and use of polynucleotide molecules for control of gene expression in plants, specifically a plant promoter, and derivatives thereof. More specifically the invention relates to a promoter used to drive expression of DNA polynucleotides in the abscission zone(s), internodes, pod walls, seeds, roots, apical meristem, and/or leaves of plants.

BACKGROUND OF THE INVENTION

One of the goals of plant genetic engineering is to produce plants with agronomically important characteristics or traits. Recent advances in genetic engineering have provided the requisite tools to transform plants to contain and express foreign genes (Kahl et al. (1995) World Journal of Microbiology and Biotechnology 11:449-460). The technological advances in plant transformation and regeneration have enabled researchers to incorporate heterologous DNA into a plant's genome where it can then be expressed in the plant cell to exhibit the added characteristic(s) or trait(s). In one approach, expression of a novel gene that is not normally expressed in a particular plant or plant tissue may confer a desired phenotypic effect, in another approach, transcription of a gene, or part of a gene could be used to suppress transcription or translation of an endogenous gene. As a further example, a gene normally expressed in a particular tissue(s) or in a particular environmental or other condition, is expressed at higher levels than normal in the tissue, or under the condition.

In order to produce such a transgenic plant, a vector that includes a heterologous DNA polynucleotide that confers a phenotype when expressed in the plant is introduced into the plant cell. The vector also includes a promoter that functions in plants, operably linked to the DNA polynucleotide, often a promoter, not normally associated with the polynucleotide. The transformed plant cell is regenerated into a transgenic plant wherein the promoter controls expression of the introduced DNA polynucleotide to which the promoter is operably linked, and thus the DNA polynucleotide confers a change in some characteristic(s) of the plant. Isolated plant promoters are, therefore, useful tools for modifying plants to have desired phenotypic characteristics.

Because the promoter is a regulatory element that plays an integral part in the expression of a DNA polynucleotide, it would be advantageous to have a variety of promoters capable of selectively directing gene expression such that a DNA polynucleotide is transcribed efficiently at the selected time during plant growth and development, in the plant or portion thereof, and in the amount necessary to produce an effect. In one case, for example, it may be beneficial to have a gene product produced at a certain developmental stage, or in response to certain environmental or chemical stimuli.

A variety of different types or classes of promoters can be used for plant genetic engineering. Promoters can be classified on the basis of range or tissue specificity. For example, promoters referred to as constitutive promoters are capable of transcribing operably linked DNA polynucleotides efficiently and expressing the DNA polynucleotides in multiple tissues. Tissue-enhanced or tissue-specific promoters are operably linked to DNA polynucleotides normally transcribed in higher levels in certain plant tissues or specifically in certain plant tissues.

Relevant to this invention are promoters that provide enhanced expression in the abscission zone, apical meristem, roots, pod wall, and leaves of a plant. The abscission zone is a region of a plant wherein the production of hydrolytic enzymes lead to cell separation (Clements, *American Journal of Botany* 88:31 (2001)), which in turn leads to the shedding of leaves, flower, fruits and/or other plant parts. The process of abscission is well described in a review by Jane Taylor and Catherine Whitelaw (*New Phytologist* 151:323, 2001); "Abscission is the term used to describe the process of natural separation of organs from the parent plant. This may be part of the highly programmed development of a plant, or in response to environmental stress. It enables temperate plants to overwinter and hence survive, but in agricultural or horticultural environments premature abscission can lead to significant crop losses." Promoters used to express genes that affect this process could be useful in modulating the loss of leaves, flowers, fruits and/or other plant parts and could lead to altered characteristics of the plant. In addition, the expression of genes in the abscission zone(s), and/or other key developmental organs and/or signaling pathways, provides scientists the ability to test approaches for increasing yield, abiotic and biotic stress tolerance, disease resistance, herbicide tolerance and resistance, and myriad other traits of agronomic importance.

Also of relevance are promoters that drive expression of genes in the apical meristem, pod wall, root, leaves, and/or flower of plants. Expression of DNA polynucleotides in these tissues could be useful to create plants with improved agronomic characteristics, including but not limited to increased yield.

By identifying and isolating a variety of plant promoters with desirable and/or unique gene expression patterns, it will be possible to operably link these promoters to DNA polynucleotides that provide advantageous agronomic effects in transgenic plants and plant cells.

Breeding permits the introduction of multiple traits into a single crop plant, also known as a gene stacking approach. In this approach, multiple genes conferring different characteristics of interest are introduced into a plant. It may be desirable when introducing multiple genes into a plant that each gene is modulated or controlled for the desired expression and that the promoter, and other regulatory elements, are diverse, to reduce the potential of gene silencing. Gene stacking can also be achieved through the introduction of a single covalently linked DNA polynucleotide that contains more than one promoter operably linked to more than one gene of interest, or with other promoter:gene combinations at different tDNA insertion sites, into a plant through transformation. It is contemplated that a plant comprising a recombinant DNA molecule of the present invention may be crossed, or stacked, with other traits such as herbicide resistance.

SUMMARY OF THE INVENTION

The present invention provides an isolated promoter polynucleotide capable of initiating and/or modulating transcription of a DNA polynucleotide to which it is operably linked. The isolated promoter polynucleotide is characterized by its ability to create recombinant DNA molecules for selectively modulating expression of any operably linked DNA polynucleotide preferentially in the abscission zone, root, pod wall, apical meristem, leaves, and/or flower of a plant.

In one embodiment, the present invention provides an isolated polynucleotide comprising SEQ ID NO: 1 or its complement; or a fragment, region, cis elements, or polynucleotides related to SEQ ID NO: 1, that function as promoters in plants. Further, it provides a promoter of the present invention which directs transcription in any plant tissue selected from the group consisting of an abscission zone or zones, root, pod wall, apical meristem, seeds, and flower.

The invention further provides recombinant DNA constructs comprising a plant promoter of the present invention operably linked to a heterologous DNA polynucleotide.

The invention further provides a method for modulating a trait of agronomic interest by incorporating a recombinant DNA molecule containing the promoter of the present invention operably linked to a DNA polynucleotide that encodes an isopentyl transferase or an ethylene receptor (or mutants thereof) into the plant's genome.

The invention further provides transgenic plants wherein said recombinant DNA molecule confers a phenotype which includes but is not limited to increased pod number per plant, stem, and/or per raceme, increased seed number per plant, decreased flower abscission, decreased pod abscission, increased plant biomass, enhanced photosynthesis, increased branching including more and longer branches, more nodes, more nodes with branches as well as longer branches, longer reproductive period, delayed senescence, changing maturity, enhanced nitrogen fixation, enhanced nodule size and/or number, enhanced abiotic stress tolerance, enhanced water use efficiency, enhanced yield, enhanced yield stability, and changes in quality traits.

It is also envisioned that a desired phenotype may be obtained through the use a recombinant DNA molecule containing a plant promoter of the present invention utilizing a gene suppression strategy, including but not limited to, RNAi or antisense technology.

The invention also provides methods for isolating the promoter described in SEQ ID NO: 1 and other related promoters of the present invention that provide the same or similar functionality with respect to expression patterns.

The foregoing and other aspects of the present invention will become apparent from the following detailed description and accompanying drawings and sequence listings.

BRIEF DESCRIPTION OF THE DRAWINGS

FIG. 10 shows a picture of transgenic and non-transgenic soybean. Note the difference in pods and other phenotypes between the plants.
FIG. 11 shows an agarose gel depicting the different products produced from RT-PCR. Note that IPT is expressed in this plant.
FIG. 12 shows the changes in a number of phenotypes between the transgenic and non-transgenic soybean plants.
FIG. 13 shows the change in important phenotypes such as node number in transgenic and non-transgenic soybean.
FIG. 14 shows changes in node and branch number in a growth chamber assay.
FIG. 15 shows the difference in pod set and seed production in a growth chamber assay. Note increase in both in plants containing the promoter of this invention.
FIG. 16 shows the phenotypes of a large number of different plants in the growth chamber assay.
FIG. 17 shows a Northern blot of the expression pattern of the endogenous gene transcribed by the A6 promoter in soybean. Note expression in flowers, apical meristem, abscission zones, and other tissues.

DETAILED DESCRIPTION OF THE INVENTION

Figure 1:
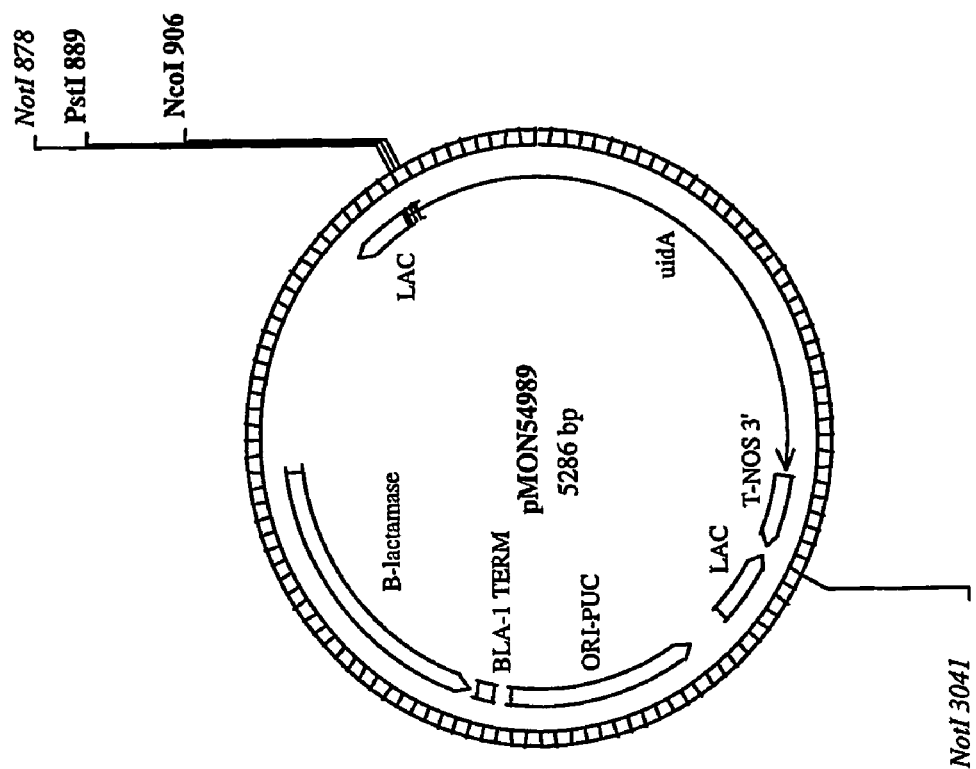
FIG. 1 shows a plasmid map for pMON54989.

The present invention provides a promoter that can direct transcription of an operably linked DNA polynucleotide in a plant. The DNA promoter encompasses the promoter as provided and cis elements, truncations, deletions and related sequences that function to direct transcription of an operably linked DNA polynucleotide in a plant. The promoter is described as an isolated polynucleotide and as part of a recombinant DNA polynucleotide. The promoter described herein allows transcription in the abscission zone(s), root, pod wall, apical meristem, leaves, and flower of plants, and may function in other tissues.

"Promoter" refers to a DNA polynucleotide that binds an RNA polymerase (often indirectly through other transcription factors) and promotes transcription of a downstream DNA polynucleotide. The downstream DNA polynucleotide can be transcribed into an RNA that has function, such as rRNA, RNAi, dsRNA, or tRNA. Often, the RNA produced is a hetero-nuclear (hn) RNA that has introns which are spliced out to produce an mRNA (messenger RNA). A "plant promoter" is a native or non-native promoter that is functional in plant cells.

Promoters are typically comprised of multiple distinct "cis-acting transcriptional regulatory elements," or simply "cis-elements," each of which can confer a different aspect of the overall control of gene expression (Strittmatter and Chua, Proc. Nat. Acad. Sci. USA 84:8986-8990, 1987; Ellis et al., EMBO J. 6:11-16, 1987; Benfey et al., EMBO J. 9:1677-1684, 1990). "cis elements" bind trans-acting protein factors that regulate transcription. Some cis elements bind more than one factor, and transacting transcription factors may interact with different affinities with more than one cis element (Johnson and McKnight, Ann. Rev. Biochem. 58:799-839, 1989). Enhancers act to upregulate the transcriptional initiation rate of RNA polymerase at a promoter, repressors act to decrease said rate. In some cases the same elements can be found in a promoter and an enhancer or repressor. In some cases enhancers can be used to change which tissues promoters drive expression within, broadening and/or otherwise changing expression patterns. The inventors have contemplated adding enhancer elements, either in close juxtaposition or at a further site separated from the promoter, in order to change or otherwise modulate transcription from the promoter that is part of the invention.

Cis elements can be identified by a number of techniques, including deletion analysis, i.e., deleting one or more nucleotides from the 5' end or internal to a promoter; DNA binding protein analysis using DNAse I footprinting, methylation interference, electrophoresis mobility-shift assays (EMSA or gel shift assay), in vivo genomic footprinting by ligation-mediated PCR, and other conventional assays; or by sequence similarity with known cis element motifs by conventional sequence comparison methods. The fine structure of a cis element can be further studied by mutagenesis (or substitution) of one or more nucleotides or by other conventional methods. See, e.g., Methods in Plant Biochemistry and Molecular Biology, Dashek, ed., CRC Press, 1997, pp. 397-422; and Methods in Plant Molecular Biology, Maliga et al., eds., Cold Spring Harbor Press, 1995, pp. 233-300. Polynucleotide regions comprising "cis elements" or "cis elements" of the polynucleotides of SEQ ID NO: 1 can be identified using computer programs designed specifically to identify cis elements, domains, or motifs within polynucleotides by a comparison with known cis elements or can be used to align multiple 5' regulatory polynucleotides to identify novel cis elements. Activity of a cloned promoter or putative promoter (cloned or produced in any number of ways including but not limited to; isolation form an endogenous piece of genomic DNA directly cloning or by PCR; chemically synthesizing the piece of DNA) can be tested in any number of ways including testing for RNA (Northern, Taqman®, quantitative PCR, etc.) or production of a protein with an activity that is testable (i.e. GUS, chlorempenicaol acetyl transferase (CAT)).

The promoter as described herein also includes plant promoters that are related to the plant promoter described. This relationship can be determined either through percent sequence identity or hybridization.

Hybridization conditions are dependent on the sequence of the polynucelotide and will be different in different circumstances. As used herein "stringent conditions" are selected to be about 5° C. lower than the thermal melting point (Tm) for the specific polynucleotide at a defined ionic strength and pH. The "thermal melting point" is the temperature (under defined ionic strength and pH) at which 50% of a target molecule hybridizes to a completely complementary molecule. Appropriate stringent conditions which promote DNA hybridization, for example, 6.0× sodium chloride/sodium citrate (SSC) at about 45° C., followed by a wash of 2.0×SSC at 50° C., are known to those skilled in the art or can be found in *Current Protocols in Molecular Biology*, John Wiley & Sons, N.Y. (1989), 6.3.1-6.3.6, incorporated herein by reference in its entirety. For example, the salt concentration in the wash step can be selected from a low stringent condition of about 2.0×SSC at 50° C. to a high stringency of about 0.2×SSC at 50° C. In addition, the temperature in the wash step can be increased from low stringent conditions at room temperature, about 22° C., to high stringent conditions at about 65° C. Both temperature and salt concentration may be varied, or either the temperature or the salt concentration may be held constant while the other variable is changed. For the purposes of this disclosure, stringent conditions include at least one wash in 2.0×SSC at a temperature of at least about 50° C. for 20 minutes, or equivalent conditions.

"Percentage sequence identity" is determined by comparing two optimally aligned sequences over a comparison window, wherein the portion of the polynucleotide or amino acid sequence in the comparison window may comprise additions or deletions (i.e., gaps) as compared to the reference sequence (which does not comprise additions or deletions) for optimal alignment of the two sequences. The percentage is calculated by determining the number of positions at which the identical polynucleotide base or amino acid residue occurs in both sequences to yield the number of matched positions, dividing the number of matched positions by the total number of positions in the window of comparison and multiplying the result by 100 to yield the percentage of sequence identity.

A plant promoter that is related to a DNA or protein sequence, for example SEQ ID NO:1 if, when optimally aligned (with appropriate nucleotide insertions or deletions totaling less than 75 percent of the reference sequence over the window of comparison) with the other polynucleotide or polypeptide (or its complementary strand); there is about 25% nucleotide equivalence; more preferably 30%; more preferably 40%; more preferably 45%; more preferably 50%; more preferably 55%; more preferably 60%; more preferably 65%; more preferably 70%; more preferably 75%; more preferably 80% equivalence; more preferably 85% equivalence; more preferably 90%; more preferably 95%; more preferably 98% equivalence; or more preferably 100% over a comparison window of at least 20 nucleotide positions; more preferably 50 nucleotide positions, more preferably 100 nucleotide positions; over more preferably the entire length of the first polynucleotide or polypeptide. Optimal alignment of sequences for aligning a comparison window may be conducted by algorithms; preferably by computerized implementations of these algorithms (for example, the Wisconsin Genetics Software Package Release 7.0-10.0, Genetics Computer Group, 575 Science Dr., Madison, Wis.). SEQ ID NO: 1 may be the full-length molecule or a portion of the longer molecule. Fragments or portions of SEQ ID NO: 1 that could function in the invention include nucleotides 100-1160, nucleotides 500-1160, nucleotides 750-1160, nucleotides 500-1000, nucleotides 250-750, nucleotides 1-500, nucleotides 1-750, nucleotides 1-1000, and nucleotides 1-1100.

Mutagenesis may be carried out at random and the mutagenized polynucleotides screened for function by procedures known in the art. Alternatively, particular polynucleotides which provide the disclosed promoter with desirable expression characteristics could be identified and these or similar polynucleotides introduced into other related or non-related polynucleotides via mutation. Similarly, non-essential elements may be deleted without significantly altering the function of the elements. It further is contemplated that one could mutagenize these polynucleotides in order to enhance their utility in expressing transgenes in a particular species, for example, in soybean.

The promoters of the instant invention can be isolated. An "isolated" polynucleotide or DNA molecule is substantially separated or purified away from other polynucleotides with which the polynucleotide is normally associated in the cell of the organism in which the polynucleotide naturally occurs, i.e., other chromosomal or extrachromosomal DNA. The term embraces polynucleotides that are biochemically purified so as to substantially remove contaminating polynucleotides and other cellular components. The term also applies to recombinant polynucleotides and chemically synthesized polynucleotides.

This promoter can be used to create any number of recombinant DNA molecules. These recombinant DNA molecules generally have a DNA polynucleotide operably linked to the promoter such that the promoter binds transcription factors and recruits an RNA polymerase to the promoter causing the creation of an RNA molecule from the operably linked DNA polynucleotide.

Genes, anti-sense RNAs, RNAi, mRNAs, or other functional RNAs could be expressed by a promoter of the instant invention, potentially any DNA polynucleotide could be operably linked to the promoter of this invention, including a coding region which encodes a protein that causes enhanced grain composition or quality, nutrient transporter functions, enhanced nutrient utilization, enhanced environment or stress resistance, a selectable marker phenotype, a screenable marker phenotype, a negative selectable marker phenotype, or altered plant agronomic characteristics (including changing cytokinin amounts for this purpose). Genes could also include, but would not be limited to, transcription factors such as Aintegumenta (ANT) (WO02059332A3, herein incorporated by reference), or genes in the ethylene biosynthesis pathway such as ETR1 (and mutants thereof), or plant hormone receptors and signaling molecules, or cytokinin producing enzymes, or glyphosate oxidoreductase or where the selected coding region encodes a protein imparting a selectable marker phenotype such as the group consisting of phosphinothricin acetyltransferase, glyphosate resistant EPSPS, aminoglycoside phosphotransferase, hygromycin phosphotransferase, neomycin phosphotransferase, dalapon dehalogenase, bromoxynil resistant nitrilase, anthranilate synthase.

A specific embodiment of the invention is directed to increasing the retention of flowers, boles, and/or pods in plants, particularly soybeans and cotton, by altering the biosynthesis or metabolism of cytokinins in/or and around the pedicel abscission zone. In one embodiment the instant invention involves the use of a promoter of the instant invention and an isopentenyl transferase gene or other genes that regulate cytokinin production, metabolism, and/or signaling. Another specific approach involves the use of a promoter disclosed herein (or another pedicel abscission zone enhanced promoter) driving the expression of genes in the ethylene biosynthetic sensing and response pathway and mutants thereof, such as ETR1 and mutants thereof.

"Isopentyl transferase" or "isopentenyl transferase" or "IPT" or "ipt" as used herein includes any enzyme that catalyzes the reaction of adenosine 5'-monphosphate and dimethylallyl disphosphate to $N^6$-($\Delta^2$-isopentenyl)adenosine 5'-phosphate, including but not limited to all isopentenyl transferase/dimethylallyl transferase from all sources including plants, animals, and microbes (Buchanan, et al., Biochemistry and Molecular Biology of Plants, Courier Companies, Inc., USA, ISBN 0-943088-39-9). "Isopentyl transferase" or "isopentenyl transferase" or "IPT" or "ipt" as used herein includes any enzyme which functions as described in FIG. 1 (p. 355) of Haberer and Kieber, *Plant Physiology* 128:354 (2002). "Isopentyl transferase" or "isopentenyl transferase" or "IPT" or "ipt" also includes any enzyme that increases cytokinin levels through a pathway which includes zeatinriboside-5'-monphosphate (ZMP) (Astot, et al, *PNAS* 97:14778-14883, 2000). IPT genes expected to function in the invention include, but are not limited to, for example, proteins which contain the motif found in many IPT genes (SEQ ID NO: 28). Proteins with other motifs, such as PF01715 (IPPT; from Pfam 12.0) and PF01745 (IPT; from Pfam12.0) are also expected to function in the invention. These latter motifs are from Pfam which describes IPT and IPPT as follows—IPT or isopentenyl transferase/dimethylallyl transferase synthesizes isopentenyladensosine 5'-monophosphate, a cytokinin that induces shoot formation on host plants infected with the Ti plasmid. IPPT is a family of IPP transferases (EC:2.5.1.8) also known as tRNA delta(2)-isopentenylpyrophosphate transferase, these enzymes modify both cytoplasmic and mitochondrial tRNAs at A(37) to give isopentenyl A(37). Pfam is a large collection of multiple sequence alignments and hidden Markov models covering many common protein families. Pfam version 12.0 (January 2004) contains alignments and models for 7316 protein families, based on the Swissprot 42.5 and SP-TrEMBL 25.6 protein sequence databases.

The term "recombinant DNAs" or "recombinant DNA molecules" as used herein means DNAs that contains a genetically engineered modification through manipulation via mutagenesis, restriction enzymes, and the like. The polynucleotide itself can come from either naturally occurring sources or can be created in the laboratory. It can also include all vectors created by DNA engineering, for example, all the DNA molecules included herein designated by pMON. For example, it can include molecules containing naturally occurring DNA or cDNA, or DNA molecules of synthetic origin in a plasmid, or isolated DNA. A "recombinant" polynucleotide or "recombinant DNA molecule" can be made by an artificial combination of two otherwise separated segments of a polynucleotide, e.g., by chemical synthesis or by the manipulation of isolated segments of polynucleotides by genetic engineering techniques. Techniques for nucleic-acid manipulation are well-known (see, e.g., Sambrook et al., Molecular Cloning, A Laboratory Manual, Cold Spring Harbor Press, Plainview, N.Y. (1989); and Ausubel et al., Current Protocols in Molecular Biology, John Wiley & Sons, New York, N.Y. (1988). The terms "recombinant DNA construct", "recombinant vector", "expression vector" or "expression cassette" refer to any agent such as a plasmid, cosmid, virus; BAC (bacterial artificial chromosome), autonomously replicating polynucleotide, phage, or linear or circular single-stranded or double-stranded DNA or RNA polynucleotide, derived from any source, capable of genomic integration or autonomous replication, comprising a DNA molecule in which one or more DNA polynucleotides have been linked in a functionally operative manner.

"Heterologous" sequence or polynucleotide refers to a polynucelotide which originates from a foreign source or species or, if from the same source or species, is modified from its original form; for example, a gene from a fungus being expressed in a plant; or a gene from the same species present under a different promoter, or a promoter driving the expression of a gene or RNA in a non-native location within the genome. It also expressly includes a native promoter/gene combination wherein either the gene or promoter is modified from its native form.

A first polynucleotide is "operably linked" with a second polynucleotide when the polynucleotides are so arranged that the first polynucleotide affects the function of the second polynucleotide. Often, the two polynucleotides are part of a single contiguous polynucleotide molecule and sometimes are adjacent. For example, a promoter is operably linked to a gene if the promoter regulates or mediates transcription of the gene. A promoter is "naturally operably linked" to a structural gene if the promoter drives the transcription of the structural gene in the genome of an organism when said promoter and said structural gene are in their native locations within said genome.

Recombinant DNA molecules comprising a promoter of the instant invention can be used to transform plants.

The promoter of the invention, when operably linked to another polynucleotide, could have utility when transformed into any type of plant, including a monocotyledonous or dicotyledonous plant. Examples of monocotyledonous plants include wheat, maize, rye, rice, oat, barley, turfgrass, sorghum, millet and sugarcane. In one embodiment of the invention, the monocotyledonous plant is maize. Examples of dicotyledonous plants include tobacco, tomato, potato, soybean, cotton, canola, alfalfa, sunflower, and cotton. In one embodiment of the invention the dicotyledonous plant is a soybean plant. The transgenic plant prepared in accordance with the invention may be of any generation, including a fertile, partially sterile, or sterile $R_0$ transgenic plant as well as seeds thereof, wherein the seed comprises SEQ ID NO: 1, or a fragment, portion, part, or cis element thereof. Also included within the invention are progeny plants of any generation such as fertile $R_0$ transgenic plant, wherein the progeny plant comprises SEQ ID NO: 1, or a fragment, portion, part, or Cis (cis) element thereof, as well as seed of a progeny plant.

In a preferred embodiment of the invention, a transgenic plant comprising a heterologous promoter of the instant invention, or a transgenic plant comprising a recombinant DNA molecule of the instant invention is produced. Various methods for the introduction of a desired polynucleotide encoding the desired protein into plant cells are available and known to those of skill in the art and include, but are not limited to: (1) physical methods such as microinjection, electroporation, and microprojectile mediated delivery (biolistics or gene gun technology); (2) virus mediated delivery methods; and (3) *Agrobacterium*-mediated transformation methods.

The most commonly used methods for transformation of plant cells are the *Agrobacterium*-mediated DNA transfer process and the biolistics or microprojectile bombardment mediated process (i.e., the gene gun). Typically, nuclear transformation is desired but where it is desirable to specifically transform plastids, such as chloroplasts or amyloplasts, plant plastids may be transformed utilizing a microprojectile mediated delivery of the desired polynucleotide.

*Agrobacterium*-mediated transformation is achieved through the use of a genetically engineered soil bacterium belonging to the genus *Agrobacterium*. A number of wild-type and disarmed strains of *Agrobacterium tumefaciens* and *Agrobacterium rhizogenes* harboring Ti or Ri plasmids can be used for gene transfer into plants. Gene transfer is done via the transfer of a specific DNA known as "T-DNA" that can be genetically engineered to carry any desired piece of DNA into many plant species.

*Agrobacterium*-mediated genetic transformation of plants involves several steps. The first step, in which the virulent *Agrobacterium* and plant cells are first brought into contact with each other, is generally called "inoculation". Following the inoculation, the *Agrobacterium* and plant cells/tissues are permitted to be grown together for a period of several hours to several days or more under conditions suitable for growth and T-DNA transfer. This step is termed "co-culture". Following co-culture and T-DNA delivery, the plant cells are treated with bactericidal or bacteriostatic agents to kill the *Agrobacterium* remaining in contact with the explant and/or in the vessel containing the explant. If this is done in the absence of any selective agents to promote preferential growth of transgenic versus non-transgenic plant cells, then this is typically referred to as the "delay" step. If done in the presence of selective pressure favoring transgenic plant cells, then it is referred to as a "selection" step. When a "delay" is used, it is typically followed by one or more "selection" steps.

With respect to microprojectile bombardment (U.S. Pat. No. 5,550,318; U.S. Pat. No. 5,538,880; U.S. Pat. No. 5,610,042; and PCT Publication WO 95/06128; each of which is specifically incorporated herein by reference in its entirety), particles are coated with polynucleotides and delivered into cells by a propelling force. Exemplary particles include those comprised of tungsten, platinum, and preferably, gold.

An illustrative embodiment of a method for delivering DNA into plant cells by acceleration is the Biolistics Particle Delivery System (BioRad, Hercules, Calif.), which can be used to propel particles coated with DNA or cells through a screen, such as a stainless steel or Nytex screen, onto a filter surface covered with monocot plant cells cultured in suspension.

Microprojectile bombardment techniques are widely applicable, and may be used to transform virtually any plant species. Examples of species that have been transformed by microprojectile bombardment include monocot species such as maize (PCT Publication WO 95/06128), barley, wheat (U.S. Pat. No. 5,563,055, specifically incorporated herein by reference in its entirety), rice, oat, rye, sugarcane, and sorghum; as well as a number of dicots including tobacco, soybean (U.S. Pat. No. 5,322,783, specifically incorporated herein by reference in its entirety), sunflower, peanut, cotton, tomato, and legumes in general (U.S. Pat. No. 5,563,055, specifically incorporated herein by reference in its entirety).

To select or score for transformed plant cells regardless of transformation methodology, the DNA introduced into the cell contains a gene that functions in a regenerable plant tissue to produce a compound that confers upon the plant tissue resistance to an otherwise toxic compound. Genes of interest for use as a selectable, screenable, or scorable marker would include but are not limited to GUS, green fluorescent protein (GFP), luciferase (LUX), antibiotic or herbicide tolerance genes. Examples of antibiotic resistance genes include the penicillins, kanamycin (and neomycin, G418, bleomycin); methotrexate (and trimethoprim); chloramphenicol; kanamycin and tetracycline.

The regeneration, development, and cultivation of plants from various transformed explants is well documented in the art. This regeneration and growth process typically includes the steps of selecting transformed cells and culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil. Cells that survive the exposure to the selective agent, or cells that have been scored positive in a screening assay, may be cultured in media that supports regeneration of plants. Developing plantlets are transferred to soil less plant growth mix, and hardened off, prior to transfer to a greenhouse or growth chamber for maturation.

The present invention can be used with any transformable cell or tissue. By transformable as used herein is meant a cell or tissue that is capable of further propagation to give rise to a plant. Those of skill in the art recognize that a number of plant cells or tissues are transformable in which after insertion of exogenous DNA and appropriate culture conditions the plant cells or tissues can form into a differentiated plant. Tissue suitable for these purposes can include but is not limited to immature embryos, scutellar tissue, suspension cell cultures, immature inflorescence, shoot meristem, nodal explants, callus tissue, hypocotyl tissue, cotyledons, roots, and leaves.

Any suitable plant culture medium can be used. Examples of suitable media would include but are not limited to MS-based media (Murashige and Skoog, Physiol. Plant, 15:473-497, 1962) or N6-based media (Chu et al., Scientia Sinica 18:659, 1975) supplemented with additional plant growth regulators including but not limited to auxins, cytokinins, ABA, and gibberellins. Those of skill in the art are familiar with the variety of tissue culture media, which when supplemented appropriately, support plant tissue growth and development and are suitable for plant transformation and regeneration. These tissue culture media can either be purchased as a commercial preparation, or custom prepared and modified. Those of skill in the art are aware that media and media supplements such as nutrients and growth regulators for use in transformation and regeneration and other culture conditions such as light intensity during incubation, pH, and incubation temperatures that can be optimized for the particular variety of interest.

A transgenic plant produced comprising a recombinant DNA molecule of the instant invention can produce a desired phenotype in the transgenic plant when compared to non-transgenic plants of the same species. Of particular interest are those plants that produce a desired phenotype related to some aspect of yield. Many phenotypes can affect "yield". For example, these could include, without limitation, plant height, pod number, pod position on the plant, number of internodes, incidence of pod shatter, grain size, efficiency of nodulation and nitrogen fixation, efficiency of nutrient assimilation, resistance to biotic and abiotic stress, carbon assimilation, plant architecture, resistance to lodging, percent seed germination, seedling vigor, and juvenile traits. These could also include, without limitation, efficiency of germination (including germination in stressed conditions), growth rate (including growth rate in stressed conditions), ear number, seed number per ear, seed size, composition of seed (starch, oil, protein) and characteristics of seed fill. "Yield" can be measured in many ways, these might include test weight, seed number per plant, seed weight, seed number per unit area (i.e. seeds, or weight of seeds, per acre), bushels per acre, tonnes per acre, tons per acre, kilo per hectare. In an embodiment, a plant of the present invention might exhibit an enhanced trait that is a component of yield.

Examples of phenotypes that could be seen in some plants comprising recombinant DNA molecules of the present invention could include changes in agronomic traits such as increased pod number per plant, stem, and/or per raceme, increased seed number per plant, decreased flower abscission, decreased pod abscission, increased plant biomass, flower number, enhanced photosynthesis, increased branching (including more and/or longer branches), more nodes, more nodes with branches, longer reproductive period, delayed senescence, changing maturity, enhanced nitrogen fixation, enhanced nodule size and/or number, enhanced abiotic stress tolerance, enhanced water use efficency, enhanced yield, enhanced yield stability, and changes in quality traits.

Many of the above phenotypes can be scored by simply counting the phenotype of interest at the appropriate stage of development, these include pod number, amount of flower abscission, amount of pod abscission, flower number, number of branches, number of nodes, reproductive period (time from flower set to senescence), time to senescence, nodule size and number, yield. Yield stability refers to the variation in yield of a plant in a number of conditions, such as over a number of years in the same field, or a number of different fields. Water use efficiency can be judged by limiting plant water, and/or measuring the water potential of the plant. Plant biomass can be judged by weighing the plants, preferably after drying, to look at dry mass of the plant. Nitrogen efficiency can be judged by limiting nitrogen input to the plant whereas not doing so to an identical plant and/or judging nitrogen content of the plant using spectroscopy or amount of photosynthesic apparatus as a judge of nitrogen content.

The laboratory procedures in recombinant DNA technology used herein are those well known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturer's specifications. These techniques and various other techniques are generally performed according to Sambrook et al., Molecular Cloning—A Laboratory Manual, 2nd. ed., Cold Spring Harbor Laboratory, Cold Spring Harbor, N.Y. (1989).

Unless otherwise noted, terms are to be understood according to conventional usage by those of ordinary skill in the art. Definitions of common terms used in molecular biology and molecular genetics can also be found in Lewin, *Genes VII*, Oxford University Press and Cell Press, New York, 2000; Buchanan, et al., *Biochemistry and Molecular Biology of Plants*, Courier Companies, USA, 2000; Lodish, et al., *Molecular Cell Biology*, W.H. Freeman and Co., New York, 2000. Common terms in genetics can be found in the prior as well as Lynch, et al., *Genetics and Analysis of Quantitative Traits*, Sinauer and Associates, Sunderland, Mass., 1998; Gonick, et al., *The Cartoon Guide to Genetics*, HarperCollins Publishers, New York, 1983; Hartwell, et al., *Genetics: From Genes to Genomes*, McGraw-Hill Companies, Boston, Mass., 2000; Hartl, et al., *Genetics: Analysis of Genes and Genomes*, Jones and Bartlett Publishers, Sudbury, Mass., 2000; Strachan, et al., *Human Molecular Genetics*, John Wiley and Sons, New York, 1999.

Having illustrated and described the principles of the present invention, it should be apparent to persons skilled in the art that the invention can be modified in arrangement and detail without departing from such principles. We claim all modifications that are within the spirit and scope of the appended claims.

All publications and published patent documents cited in this specification are incorporated herein by reference to the same extent as if each individual publication or patent application is specifically and individually indicated to be incorporated by reference.

The following examples are included to demonstrate embodiments of the invention. It should be appreciated by those of skill in the art that the techniques disclosed in the examples that follow represent techniques discovered by the inventors to function well in the practice of the invention. However, those of skill in the art should, in light of the present disclosure, appreciate that many changes can be made in the specific embodiments which are disclosed and still obtain a like or similar result without departing from the spirit and scope of the invention, therefore all matter set forth or shown in the accompanying drawings and examples is to be interpreted as illustrative and not in a limiting sense.

EXAMPLES

Example 1

An abscission zone promoter, referred to herein as A6 (SEQ ID NO: 1) was isolated from soy genomic DNA. The two primers used were dsb 68 (with a NcoI site on the 5' end of the primer)5'

```
                                        (SEQ ID NO:2)
5'  CCATGGCTTCGTTTCTTTCTTTCTTTCCTTTAATAACTG 3'
``` and dsb 69 (with a PstI site on the 5'end of the primer),5'

```
                                       (SEQ ID NO:3)
 5' CTGCAGTCACAAGACAAACCTTAAACATACCATACC 3'.
```

The template used was either genomic DNA or genomic DNA digested with Hind3 and self-ligated. 0.5 ul of each template was used to set up the PCR reaction. BMB PCR (Boehringer Mannheim, Ingelheim, Germany) kit was used to bring the concentration of PCR buffer to 1× and 0.5 ul Taq polymerase enzyme was used. 0.2 um of dNTPs and 1 ul of dsb 68 and dsb 69 (10 um each) was added. PCR conditions were as follows: 94° C. for 2 mins for 1 cycle, 94° C. for 20 sec, 58° C. for 30 sec and 72° C., for 2 min for 40 cycles with a final extension at 72° C., held forever (or in actual use, until the scientist removes the plate or tube from the PCR machine).

The amplification product was run on a 1% agarose gel. A ~1.1 kb PCR product was isolated. This product is the A6 promoter (P-A6). Using manufacturer's instruction for Zero Blunt TOPO PCR kit (Invitrogen, Cat # 190305, 25-0215) (Invitrogen Corporation, 1600 Faraday Avenue, Carlsbad, Calif. 92008), the amplification product for the A6 promoter (pA6) was cloned in a blunt vector. The ligation reaction was transformed into TOPO 10 *E. coli* cells (which is provided with the kit) and the transformation mix was spread onto LB plates containing 50 ug/ml of kanamycin. Plates were incubated overnight at 37° C.

A single colony was isolated and inoculated in 3 ml of LB containing 50 ug/ml kanamycin. Colonies were incubated in a shaking 37° C. incubator.

Miniprep was done on these colonies using Qiagen spin miniprep kit (250), cat # 27106 (Qiagen Inc. 28159 Avenue Stanford, Valencia, Calif. 91355). Instructions were followed according to the manufacturer's protocol.

DNA obtained was confirmed by sequencing with universal primers M13F and M13 R that are on the vector (not in the insert); and the gene specific primers, dsb 68 and dsb 69 (located in the cloned fragment). Sequences for M13 F are 5'

```
    Sequences for M13 F are
    5' GGTTTTCCCAGTCACGAC 3'       (SEQ ID NO:4)
    and

M13 R
    5' CACAGGAAACAGCTATGACC 3'.    (SEQ ID NO:5)
```

A large scale prep was prepared for two of the above clones using Qiagen Plasmid Midi kit (50), cat # 12144.

Ten ug of DNA was digested with Pst1 and Nco1 in a 50 ul reaction in Gibco BRL buffer 2 and 1 ul of enzymes Pst1 and Nco1 were added to the reaction (GIBCO-BRL, Gaithersburgh, Md., U.S.A.). The cloning vector used for P-A6 was pMON54989 (see FIG. 1). 5 ug of pMON54989 was digested with PstI and Nco1 using the same conditions. Both the DNA's were incubated in a 37° C. waterbath for approximately 2 hours.

The digest was then run on a 1% agarose gel. The linearized pMON54989 band with Pst1 and Nco1 sites at the end and the A6 promoter band isolated from vector was cut out of the gel. The DNA was gel purified using Qiagen's gel purification kit; (QIAquick Gel extraction kit (50), cat # 28704). A ligation reaction was set up using Rapid DNA Ligation Kit (cat # 1 635379) as follows: 10 ul of digested pMON54989, 6 ul of insert (A6 promoter) was added to a ligation reaction which contains 10 ul of 2× ligation buffer and 1 ul of ligase, 5 units/ul. The reaction was ligated at RT for 15 minutes. 2 ul of this ligation reaction was transformed into 100 ul of Max Efficiency DH5α Competent Cells, from Gibco-BRL, cat # 18258-012. The transformation mix was spread onto LB plates containing 100 ug/ml of ampicillin. Plates are incubated overnight at 37° C.

A single colony was isolated and inoculated into 3 ml of LB containing 100 ug/ml ampicillin. Colonies were incubated at 37° C. in a shaking incubator.

Figure 2:
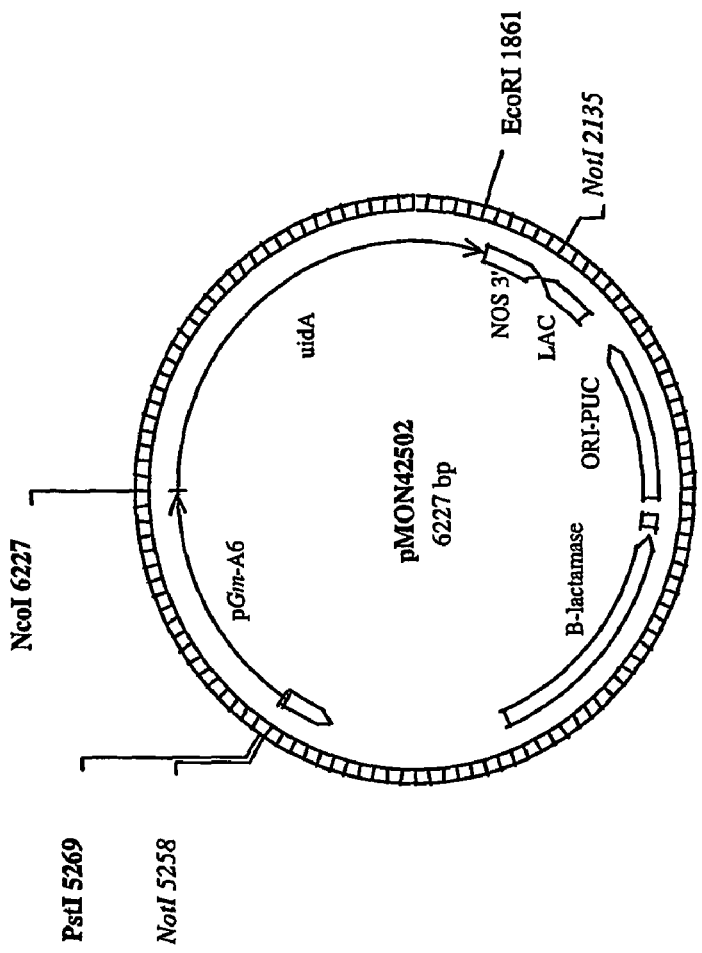
FIG. 2 shows a plasmid map of pMON42502.

A miniprep was done on the colonies using Qiagen spin miniprep kit (250), cat #27106 (Qiagen Inc. 28159 Avenue Stanford, Valencia, Calif. 91355) (as per manufacturer's protocol). To confirm the presence of insert in the DNA, 5 ul of the minprep DNA was digested with Pst1 and Nco1 and run on an agarose gel. The DNA prep showed the 1.1 kb band, indicating it had the promoter in it. A large scale prep was prepared for the positive clone. This shuttle vector used is called pMON42502 (FIG. 2). This has the P-A6 driving GUS as the transgene with NOS 3' as the terminator.

A large-scale prep was prepared for two of the above clones for pMON42502, using Qiagen Plasmid Midi kit (50), cat # 12144. This was digested with Not1 to obtain the region: P-A6-GUS-NOS. This insert was inserted into a 2T vector, pMON 41162 at Not1 site (FIG. 3). pMON41162 (FIG. 3) is the binary vector used for transformation.

DNA for pMON41162 had been previously digested with Not1 using Gibco-BRL enzyme Not1. After the digestion was completed, the 5' end was de-phosphorylated to prevent self-ligation. This reaction was done in the presence of 1× phosphatase buffer and 1 unit of Calf Intestinal Alkaline Phoshatase enzyme (BMB, cat # 18009-019). Manufacturer's instructions were followed.

DNA for pMON42502 was also digested with Not1, as above. After the digestion was complete, both reactions were run on an agarose gel. DNA was extracted from the gel for both pMON 42502 and pMON 41162. A ligation reaction was set up as follows: 2 ul of de-phosphorylated pMON41162, 6 ul of insert from pMON42502 was added to a ligation reaction which also contained 10 ul of 2× ligation buffer and 1 ul of ligase, 5 units/ul. The reaction is ligated at RT for 15 minutes. 2 ul of this ligation reaction is transformed into 100 ul of Max Efficiency DH5αCompetent Cells, from Gibco-BRL, cat # 18258-012. The transformation mix was spread onto LB plates containing 50 ug/ml of streptomycin. Plates are incubated overnight at 37° C.

Figure 4:
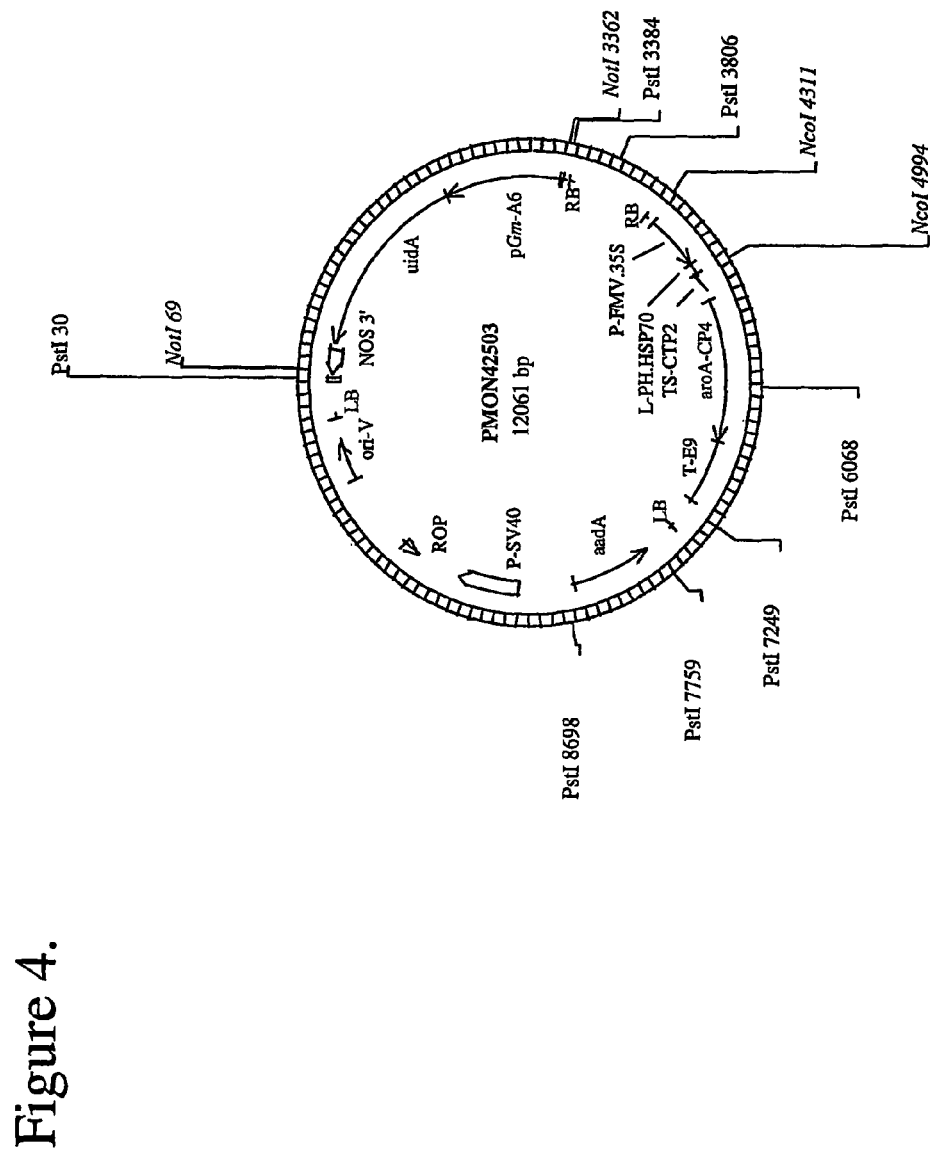
FIG. 4 shows a plasmid map of pMON42503.

A miniprep was done on the colonies using Qiagen spin miniprep kit (250), cat #27106 (Qiagen Inc. 28159 Avenue Stanford, Valencia, Calif. 91355). Instructions were followed according to the manufacturer's protocol. To confirm the presence of insert in the DNA, 5 ul of the minprep DNA was digested with Not1. The digested DNA prep that showed ~3 kb band indicates it has P-A6-GUS-NOS insert in it. A largescale prep was prepared on two clones, using Qiagen Plasmid Midi kit (50), cat # 12144. This vector is called pMON42503 (FIG. 4). The plasmid was checked with six different enzymes to determine the orientation of the P-A6-GUS-NOS in pMON41162. An orientation where both the P-A6 and P-FMV.35S are located at the right border (RB) of the cassette was preferred and selected. The correct orientation was also confirmed by sequencing the junctions between the ligated portions. The vector created was called pMON42503 (FIG. 4).

Example 2

PMON42503 was transformed into soybean using the following method. Dry A3244 soybean seeds were germinated by soaking in sterile distilled water (SDW) for three minutes, drained and allowed to slowly imbibe for 2 hours at which time Bean Germination Media (BGM) was added. At approximately 12 hours, seed axis explants were isolated by removing seed coats and cotyledons. Inoculation occurred 14 hours after the addition of SDW.

Explants were placed into sterile Plantcons with 20 mL of the plasmid being transformed and resuspended to an optical density A660 of approximately 0.3 in ⅒ Gamborg's B5 media (Gamborg et al., Exp. Cell Res., 50:151-158, 1968) containing 3% glucose, 1.68 mg/L BAP, 3.9 μL MES, 0.2M acetosyringone, 1 mM galactronic acid, and 0.25 mg/L GA3. Each Plantcon was sonicated for 20 seconds in a L&R Quantrex S140 sonicator that contained SDW+0.1% Triton X100 in the bath. Plantcons were held in place at approximately 2.5 cm below the surface of the bath liquid. Following sonication, explants were inoculated for an additional hour while shaking gently on an orbital shaker at ~90 RPM. After inoculation, the *Agrobacterium* was removed. One sheet of square filter paper and 3 mL of co-culture media containing 0-500 mM lipoic acid were added. Co-culture media consisted of ⅒ Gamborg's B5 media containing 5% glucose, 1.68 mg/L BAP, 3.9 μL, 0.2M acetosyringone, 1 mM galactronic acid and 0.25 mg/L GA3. Explants were incubated at 23° C., dark for 3 days.

Shoots were cut 5-8 weeks post-inoculation and rooted on Bean Rooting Media (BRM) containing 25 mM glyphosate and 100 mg/L Timetin.

| BEAN GERMINATION MEDIA (BGM 2.5%) | |
|---|---|
| COMPOUND: | QUANTITY PER LITER |
| BT STOCK #1 | 10 mL |
| BT STOCK #2 | 10 mL |
| BT STOCK #3 | 3 mL |
| BT STOCK #4 | 3 mL |
| BT STOCK #5 | 1 mL |
| SUCROSE | 25 g |

Adjust to pH 5.8.
DISPENSED IN 1 LITER MEDIA BOTTLES, AUTOCLAVED

| ADDITIONS PRIOR TO USE: | PER 1 L |
|---|---|
| CEFOTAXIME (50 mg/mL) | 2.5 mL |
| FUNGICIDE STOCK | 3 mL |

BT Stock for Bean Germination Medium (BGM)

Make and store each stock individually. Dissolve each chemical thoroughly in the order listed before adding the next. Adjust volume of each stock accordingly. Store at 4° C.

| Bt Stock 1 (1 liter) | |
|---|---|
| KNO3 | 50.5 g |
| NH4NO3 | 24.0 g |
| MgSO4*7H2O | 49.3 g |
| KH2PO4 | 2.7 g |
| Bt Stock 2 (1 liter) | |
| CaCl2 *2H2O | 17.6 g |
| Bt Stock 3 (1 liter) | |
| H3BO3 | 0.62 g |
| MnSO4-H2O | 1.69 g |
| ZnSO4-7H2O | 0.86 g |
| KI | 0.083 g |
| NaMoO4-2H2O | 0.072 g |

| -continued | |
|---|---|
| CuSO4-5H2O | 0.25 mL of 1.0 mg/mL stock |
| CoCl4-6H2O | 0.25 mL of 1.0 mg/mL stock |
| Bt Stock 4 (1 liter) | |
| Na2EDTA | 1.116 g |
| FeSO47H2O | 0.834 g |
| Bt Stock 5 (500 mL) Store in a foil wrapped container | |
| Thiamine-HCl | 0.67 g |
| Nicotinic Acid | 0.25 g |
| Pyridoxine-HCl | 0.41 g |
| FUNGICIDE STOCK (100 mL) | |
| chlorothalonile (75% WP) | 1.0 g |
| benomyl (50% WP) | 1.0 g |
| captan (50% WP) | 1.0 g |
| Add to 100 mL of sterile distilled water. | |
| Shake well before using. | |
| Store 4° C. dark for no more than one week. | |
| BEAN ROOTING MEDIA (BRM) (for 4 L) | |
| MS Salts | 8.6 g |
| Myo-Inositol (Cell Culture Grade) | .40 g |
| Soybean Rooting Media Vitamin Stock | 8 mL |
| L-Cysteine (10 mg/mL) | 40 mL |
| Sucrose (Ultra Pure) | 120 g |
| pH 5.8 | |
| Washed Agar | 32 g |

Additions After Autoclaving:

| ADDITIONS AFTER AUTOCLAVING: | |
|---|---|
| BRM Hormone Stock | 20.0 mL |
| Ticarcillin/clavulanic acid (100 mg/mL Ticarcillin) | 4.0 mL |
| VITAMIN STOCK FOR SOYBEAN ROOTING MEDIA (1 liter) | |
| Glycine | 1.0 g |
| Nicotinic Acid | 0.25 g |
| Pyridoxine HCl | 0.25 g |
| Thiamine HCl | 0.05 g |

Dissolve one ingredient at a time, bring to volume, store in foil-covered bottle in refrigerator for no more than one month
BRM HORMONE STOCK
Amount for 1 liter
6.0 mL IAA (0.033 mg/mL)
4.0 mL SDW
Store dark at 4° C.

Example 3

GUS Assays on Plant Tissues

R1 seeds from fifteen events containing the construct pMON42503 were obtained. Twenty seeds were planted for each event in Metro Mix (Scotts, Maryville, Ohio) soil in a green house. Two leaf punches were taken for each of the samples at the first trifoliate stage. One leaf punch was used for CP4 Elisa assay and another for a PCR reaction. The PCR assay was done with two sets of primers; one set of primers is on the 3' end of A6 promoter and the other primer on GUS towards its 5' end; the other set of primers is on P-FMV.35S towards 3' end and on CP4 towards 5' end. The use of these two PCR assays will help identify lines that are positive for the transgene and CP4. This result coupled with the CP4 Elisa assay will be used to validate events that are free from the marker.

PCR Assay:

A single leaf punch was collected using a standard one-hole paper punch. The plant tissue was collected frozen in a 96-well format container. To extract DNA, REDExtract-N-Amp Plant PCR kit (Cat # XNA-P, Sigma, 3050 Spruce Street, St. Louis, Mo. 63103 USA) was used. DNA was extracted as follows; 100 ul of Extraction Solution was added to each well and the plate was covered with a plate sealer. The 96 well plate was heated to 95° C. for 10 minutes in a heat block. The plate was then cooled to room temperature and then again heated at 95° C. for 10 minutes. The plate was cooled to RT and then spun in a microfuge before removing the plate sealer. This spinning is believed to reduce contamination of DNA across wells. To each well an equal amount of Dilution buffer is added (provided in the kit). The diluted leaf extract was then stored at 2-8° C. PCR reactions were set up for each of the plates using the above leaf extract. The following reagents are added to thin walled tubes:

In a 10 ul PCR reaction, To 2 ul of the leaf disk extract add 5 ul of REDExtract N-amp PCR reaction mix is added, (this contains buffer, salts, dNTPs, Taq polymerase and Taq Start antibody) and the two sets of primers, 0.025 um of dsb 177 (hybridizes to P-A6) 5' CCCTGCCCAGATAGTTTTTCTCC 3' (SEQ ID NO: 6) and 0.025 um of JA00-22 (hybridizes to GUS) 5' CAATTGCCCGGCTTTCTTGT 3' (SEQ ID NO: 7), 0.1 um of JA00-21 (hybridizes to P-FMV.35S) 5' TGT-CAGCTTTCAAACTCTTT 3' (SEQ ID NO: 8) and 0.1 um of cp4 rt1 (hybridizes to CP4) 5' GGAGAGTTCGATCT-TAGCTCCAAG 3' (SEQ ID NO: 9), add 1 mm MgCl2 (this addition brought the concentration of MgCl2 to 2.5 mm total concentration and the volume up to 10 ul). PCR conditions were as follows; 94° C. for 2 mins then 30 cycles of 94° C. for 30 sec, 49° C. for 30 sec and 68° C. for 1½ min. The reaction was held at 10° C. until removed from machine. The PCR products were run on a 2% agarose gel to get a good separation between 450 bp and 1.6 kb PCR products (Sambrook et al., Molecular Cloning, A Laboratory Manual, Cold Spring Harbor Press, Plainview, N.Y. (1989); and Ausubel et al., Current Protocols in Molecular Biology, John Wiley & Sons, New York, N.Y. (1988).

CP4 assay:

To a single leaf punch of plant tissue add 300 ul of Elisa Incubation buffer (ELISA incubation buffer: 1×PBS, 0.5 ml Tween 20 per liter and 2 g BSA per liter) and three glass/steel beads, 3 mm size. (Note: to each 100 mls of ELISA incubation buffer used for extraction with 1 tablet of Boehringer Mannheim complete protease inhibitor cocktail #1697498.) 30 ml buffer were prepared for each plate. A capmat was placed on the plate and centrifuged (at 4 degrees C.) for 5 minutes at 2000 rpm. Plates were shaken mechanically for 2 sets of three minutes each and frozen until use.

Using coating buffer: Plates were coated with anti-CP4 EPSPS monoclonal antibody clone 38B6.2 lot #6199732 (3.2 mg/ml), diluted 1:3200 (3.125 ul per 10 ml) or at 1:6400 (Padgette, et al, Crop Sci. 35:1451-1461, 1995). Plates were covered with plastic seal and stored in a humid box or incubated at room temperature for 4 hours or overnight at 4° C. Plates were kept for up to 2 weeks in the cold. At the time of use plates were given 3 quick washes with (PBS-0.05% Tween 20). Diluted leaf samples (10 ul of a 300 ul leaf-punch extract plus 90 ul ELISA buffer) were loaded 100 uL/well. Plates were incubated at room temperature for 4 hours or overnight at 4° C. 3 Quick washes with (PBS-0.05% Tween) were done to each plate. 100 ul of HRP conjugate Goat anti-CP4-EPSPS (Lot 6558618) were diluted 1:800. Plates were incubated at RT for 2 hours at Room Temp or O/N at 4 degrees C. Plates were then washed 3× with PBS-0.05% Tween 20. 100 uL/well of TMB substrate was added and incubated for 10 minutes at RT (TMB substrate must be at room temperature prior to use). The reaction was stopped with 50 uL 3M Phosphoric Acid (Peroxidase Reaction, not AP). The plate was read on a plate reader at 450 nm-655 nm (L1-L2) for TMB substrate (CP4 ELISA).

Out of the fifteen events, three events had incorporated into their genome P-A6-GUS (promoter A6 operably linked to GUS), and were free from the marker (CP4). Seven total events had presence of marker along with P-A6-GUS.

Histochemical Localization of X-Glucuronidase:

Using a scalpel, free-hand sections were taken from pod abscission zone and leaf abscission zone of the plants described above at the R3 stage of soy development. The R3 stage is when flowers are blooming and a pod of about 0.5-1 cm is developing at the lowest nodes of the plant. The tissue was placed in 1×PBS with 0.1% Tween 20. The tissues were lightly fixed in 0.3% paraformaldehyde in 50 mM phosphate buffer, pH7.2 by vacuum infiltration. They were incubated in the fixative for one hour at RT. The tissues were washed in buffer 2-3×. The tissues were incubated in 0.5 mg/ml of X-Gluc for 12-24 hours at 37° C. (X-Glucornidase or 5-Bromo-4-chloro-3-indolyl-D-glucuronide cyclohexy-lamine salt; Rose Scientific Ltd 4027-97Street, Edmonton, Alberta, T6E 5Y5). The tissues were rinsed 3× in potassium phosphate buffer, pH7.2. Samples were then washed in gradient EtOH (10-70% and then stored in 70% EtOH; indicates that tissue is washed thru 10, 20, 30, 40, 50, 60 and 70% EtOH. Usually this is referred to as gradient EtOH washes. 10-30% EtOH washes were done for 30 mins and 40-70% EtOH were done for 60 mins respectively.). Each of these steps can be done from 30-60 minutes each.

Stained tissues were observed under the microscope. The tissue showed a specific staining pattern, enhanced in the pod abscission zones and the leaf abscission zone. This visual check was non-quantitative, further analysis was done to quantitate the expression.

GUS Assay:

Tissue were collected from leaf, pod abscission zone, leaf abscission zone, seed, pod wall, root, and internodes at R5 stage of plant development. Previous Northern studies done at this developmental stage showed the endogenous A6 gene was strongly expressed in the pod abscission zone. R5 stage is when pod is about 2-3 cm long, some flowers are in bud stage and others are senescing. Tissues were collected and frozen. Tissues were ground using a mortar and pestle in an eppendorf tube (~100 mg of tissue).

1 ml GUS assay buffer (0.1M KPO4, pH7.8, 10 mM DTT, 1 mM EDTA) was added to the ground tissue sample. The sample was spun for 10 minutes in a microfuge in a cold room.

A 1:25 dilution of the original extract was used in future steps (dilution with GUS assay buffer, as above). Dilutes samples were arranged in 96 well plate.

For Protein Assay:

Fresh BSA standards ranging between 0.5 ug to 20 ug were prepared.

For each 2-10 ul of sample, add 50 ul of Bradford dye and bring the volume up to 200 ul. The protein quantity is read at 590 nm. Make sure all the samples fall in the range between the standards; if they do not change sample dilutions so that they do fall between the standards.

For GUS Assay:

A 1:25 ul dilution (10 ul +240 ul of GUS assay buffer) of the original extract, 200 ul of 2.5 mM MUG buffer was used (4-Methylumbelliferyl α-D-Glucuronidase, MUG, # M-9130, Sigma) and added it to 50 ul of sample (1:25 dilution). The samples were read first under endpoint wavelength 355 nm and then read under kinetic at 460 nm. (Since a fluorometric substrate (MUG) was used the reaction or hydrolysis of MUG with GUS needs to be terminated by a basic solution (this is in our GUS assay buffer). When the reaction is terminated 4-methylumbelliferone (MU) is released which is a flourescent molecule into the solution, 4-MU has a peak excitation of 365 nm (UV) and a peak emission of 460 nm (blue). In order to read the fluoresence of GUS assay, the fluoresence must be capable of exciting and reading at or near these wavelenghts. (reference GUS Protocols, Chapter 3: Quantitation of GUS activity by Fluorometry by Sean R. Gallagher; Academic Press, Inc., Harcourt Brace Jovanovich, Publishers, San Diego, Calif., 92101).

The slope value from the standard reading that is obtained from endpoint reading is used for calculating GUS value. The data from the plate in Kinetic was studied using an Microsoft Excel© spreadsheet (detailed below). A standard GUS control is prepared in the range of 50-1600 pmol/MU using 4-Methylumbelliferone or 7-hydroxyl-4-methyl coumarin (# M-1508, Sigma).

GUS values were obtained from each tissue and then calculated as % of total GUS expression for that line. This was then graphed against the tissues collected to check for maximum GUS expression in the tissues. Further analysis was done (see below) prior to final data analysis.

Calculation to Obtain the Results:

The values obtained for protein per sample are multiplied by the dilution factor used for each sample to obtain value of the protein in ug/ul. Similarly, the values obtained from the fluorescence microplate reader is in mRFU divide it by 50 to calculate mRFU/ul (Fmax or fluorescence microplate reader, Molecular Devices Corporation, Sunnyvale, Calif. 94089, USA, using version P1.12 software). This mRFU value needs to be converted to RFU (by multiplying mRFU by 1000).

Calculate the concentration in pmoles in MU using the slope values. Multiply this value by 25 (dilution factor). Divide this value by the amount of protein (in ug/ul) to give pmol/MU/ug protein.

Complete GUS value data for certain events is shown below.

ml mark on the tube. 1 ml of CTAB extraction buffer (previously heated to 55-65 degrees C.) was added and vortexed with each sample so tissue is completely dissolved in the buffer (CTAB buffer: In 500 ml bring final conc of NaCl to 1.4M, EDTA to 20 mM, Tris-HCl to 100 mM (pH 8.0) and 3% w/v of CTAB. Add CTAB last and heat under medium heat until CTAB goes into solution; filter through a 0.2 u filter bottle). Place samples in a 55-65 degree C. water bath for 45 minutes (vortex tubes every 10 mins). Samples were spun at 13K for 5' and supernatants transferred to a fresh tube. An equal amount of chloroform was added to each tube, and tubes were inverted several times. Samples were spun at 13K for 5', and aqueous DNA layer is transferred to a fresh tube. Equal amount of 100% EtOH is added to each tube and tubes are inverted gently about ten times. Samples were spun at 13K for 3', and the pellet was washed in 70% EtOH and pellet dried. DNA was dissolved in 200 ul of 10 mM TE.

A digest is set up to digest the genomic DNA with a restriction enzyme that did not restrict (cut) in the construct. In this case the Sca1 enzyme was selected. 100 ul (about 5-10 ug of DNA) was digested in 500 ul volume with 50 units of enzyme. Digestion was done overnight at 37° C. The next day the digested DNA was extracted using phenol chloroform extraction, precipitated using Na-acetate and isopropanol, washed with 70% EtOH. The pellet was resuspended in 20 ul water and run with a loading dye on a 0.8% agarose gel. The gel is run at 20V overnight to obtain good separation in 1×TAB buffer. The gel was taken through the process of nicking with 0.25M HCl for 10 mins, a denaturation step in 1.5M NaCl, 0.5M NaOH for 15 minutes, twice; and lastly a neutralization step in 1.5M NaCl, 0.5M Tris-Cl pH7.2, 0.001M EDTA for 15 minutes, twice. The DNA was then transferred to nylon membrane (positively charged catalog number 1209299, Roche Molecular Biochemicals, Basel, Switzerland). DNA was transferred by a similar method 'Transfer DNA to Nitrocellulose Filters', Molecular Cloning, A Laboratory Manual-2nd Edition by Sambrook, Fritsch and Maniatis, pg 9.38-9.41. The DNA is cross-linked to the membrane on a Stratalinker (Stratagene, La Jolla, Calif., as per manufacturer).

Membranes were probed with two sets of probes, one for P-FMV.35S and the other for P-A6 (promoter of A6 gene) using a non-radioactive probing method. Probes are prepared using PCR DIG Probe synthesis kit (catalog number 1636090, Roche Molecular Biochemicals, Basel, Switzerland).

TABLE 1

| Event | leaf | Pedicel AZ | Leaf AZ | internode | podwall | seed | root |
| --- | --- | --- | --- | --- | --- | --- | --- |
| 19733 ul(n = 8) | 0.00 | 44950.39 | 973.16 | 2841.58 | 136.03 | 346.94 | 12752.65 |
| 19715 ul(n = 5) | 358.99 | 27032.82 | 20221.87 | 6213.86 | 581.74 | 1494.28 | 14375.37 |
| 19716 ul(n = 4) | 5354.93 | 312618.30 | 177251.42 | 78960.81 | 18503.61 | 7988.50 | 15283.58 |
| 35S-GUS 7346 | 5409.76 | 14419.22 | 23756.77 | 15008.75 | 12676.72 | 0.00 | 4723.00 |

Example 4

DNA Extraction by CTAB Method:

Leaf tissue is collected for each line under liquid nitrogen and stored in −80° C. freezer until use. The samples were ground using mortar and pestle in cold conditions. An eppendorf tube was filled with powdered soybean leaf tissue to a 0.5

Preparation of DIG-PCR Probe:

Reaction to prepare a P-A6-GUS probe is set up as follows with 0.1 μM conc for primers dsb 177 (SEQ ID NO: 6) 5' CCCTGCCCAGATAGTTTTTCTCC 3', dsb 184 (SEQ ID NO: 10) 5' TGTTCGGCGTGGTGTAGAGC 3' and probe for P-FMV.35S-CP4 using 0.1 um of dsb 182 (SEQ ID NO:11) 5' CAGCATTCCAGATTGGGTTCAATC 3' and dsb 187 (SEQ ID NO: 12) 5' CACGCAAGGT AACTGGAAGAC 3' were used in separate reactions with 1×DIG-PCR buffer, 200 μM conc of PCR DIG-dNTPs, 2.6 units of high Fidelity Taq polymerase, 1 ul of 1:100 diluted pMON42503 as template. PCR conditions were set as follows: 94° C. for 2 minutes then 94° C. for 30 sec, 50° C. for 30 sec, 68° C. for 1½ min for 35 cycles, then an extension at 68° C. for 10 minutes followed by a zero degree hold until the investigator.

The DNA amplification product was run on a 1% agarose gel. Bands were cut out and purified on a gel extraction column from Qiagen (QIAquick Gel extraction kit (50), cat # 28704). The amount of probe purified was estimated as per manufacturer's protocol in Roche Molecular Biochemicals, DIG Application Manual for Filter hybridization, section 2.6.2. We needed 20 ng of labeled probe per microliter.

The membranes are pre-hybridized and later hybridized with the two probes prepared above individually, as per protocols in section 3.1.2.3 and 4.1.2.1. The only change was made in diluting Anti-Digoxigenin-AP to 1:20,000 in Blocking solution. CDP-Star was used at 1:100 dilutions to visualize probe-target hybrids by chemiluminescent method. Lumi-Film (Roche) Chemiluminescent Detection Film (cat # 1666 657) to expose the membranes.

To allow further probing, probe of from a membrane used 0.2M NaOH containing 0.1% SDS twice for 15 minutes at 37° C. and membrane was rinsed in 2×SSC. The membrane can be now probed with another probe and the same procedure is followed as above.

Results of Linkage Southern:

Once both the membranes have been probed, the films are overlaid over each other. Data was interpreted as follows; if a band of the same size overlaps on each film, then those lines were identified as linked for P-FMV.35S and P-A6, in some cases where they don't overlap we have assumed that P-FMV.35S and P-A6 are on two separate chromosomes. In other cases a banding pattern was seen so that there are multiple copies of P-FMV.35S or P-A6 and only some of these bands overlap, those were thought to be linked but with multiple copies of the insert.

Using the data compiled in this and the prior examples the following table was compiled. The results show only data from unlinked (ul) events. The 35S promoter driving GUS is being used as a control in the experiment AZ stands for abscission zone. Analysis of the data shows that the promoter drives transcription in the AZ of plants, enhancing transcription in the pedicel AZ, internodes, leaf AZ, and other tissues differentially. As would be expected by one skilled in the art, different events have different patterns of expression, likely due to differing chromatin structure in different cell types at the location of the insertion. It is also possible that some events have inserted near other transcriptional control elements that are modifying transcription from the promoter. As can be seen in Table 1, the A6 promoter leads to a transcriptional pattern of generally increased transcription in the abscission zones of plants, but also transcription in the internodes and other tissues. As described herein the abscission zone transcription has specific utility as it relates to yield, but driving transcription of specific genes or functional RNAs in the other tissues (i.e. internodes) showing expression might also be useful. Variation is seen between lines, this variation is common to one skilled in the art and may come from insertion site effects as well as other sources.

Example 5

The cloning of an isopentyl transferase gene under the transcriptional control of the A6 promoter was done in 2 steps.

Step I: Preparation of pA6:IPT Intermediate

A plasmid (pMON42502; FIG. 2) DNA was digested with EcoRI. The overhangs were then filled in with Klenow enzyme. A restriction digest with NcoI was then done. This plasmid was then run on an agarose gel. A 4.36 kb band was excised and purified. This digested plasmid was ligated to the IPT gene insert (discussed below).

Figure 5:
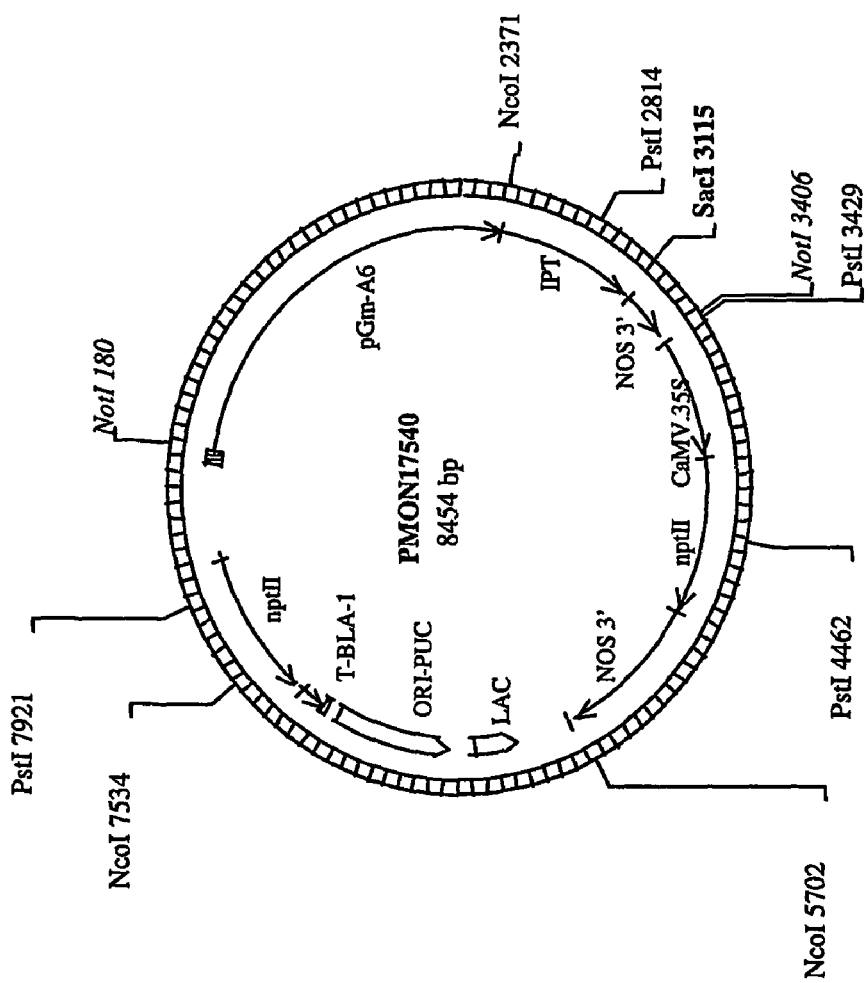
FIG. 5 shows a plasmid map of pMON17540.

To obtain IPT gene insert, pMON17540 (FIG. 5) was digested with SacI, overhangs were removed by T4 polymerase (using its inherent exonucleolytic activity), then cut with NcoI. This digest was run on an agarose gel, a 0.744 kb band (IPT gene) was excised and purified and used in the ligation with the above plasmid.

The cloning junctions of the resultant plasmid were confirmed by DNA sequencing.

Step II: Creating A6:IPT/2T Construct by Transferring the A6:IPT Cassette from the Above Intermediate into pMON42503 (FIG. 4) Backbone.

Figure 6:
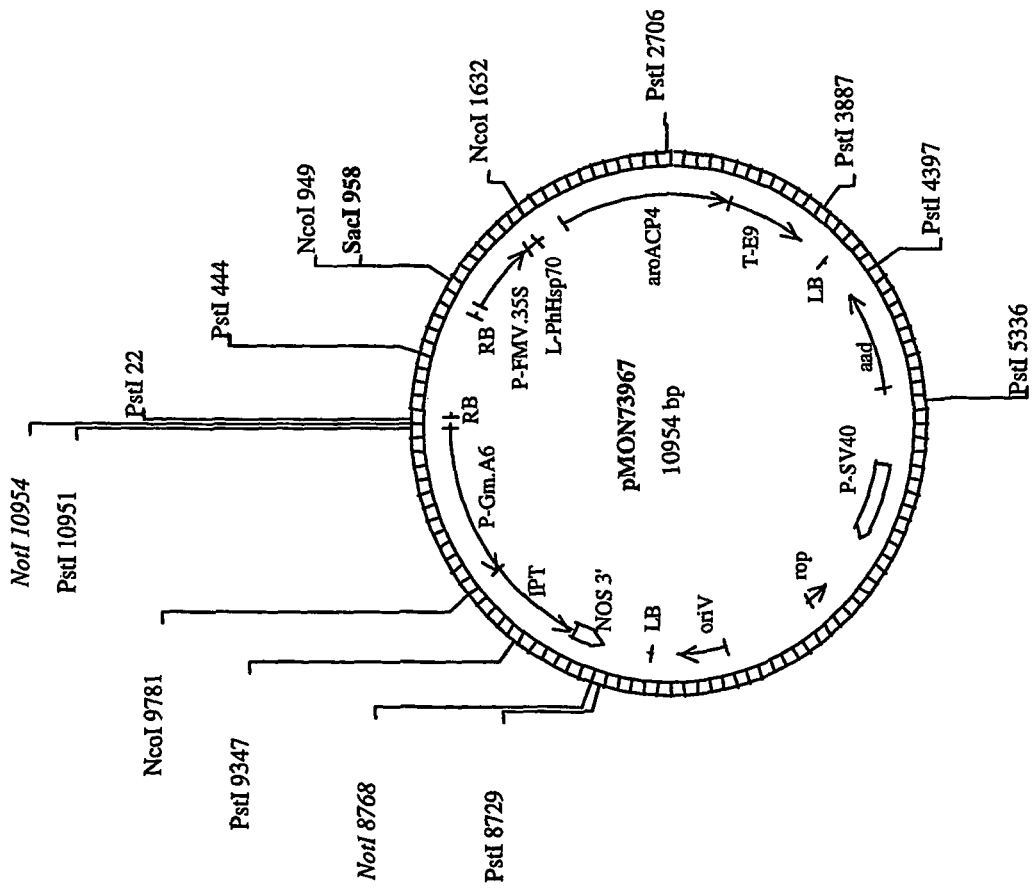
FIG. 6 shows a plasmid map of pMON73967.

PMON42503 was cut with NotI. The products were run on an agarose gel and an 8.7 kb band was excised and purified. This was used as a backbone to receive A6:IPT cassette. The above mentioned intermediate clone was digested with NotI and 1.98 kb band was excised, purified, and ligated to pMON42503 backbone. This clone was confirmed by restriction mapping and transformed into plants as in Example 2. The clone is named pMON73967 (FIG. 6).

Example 6

To Create an pA6-etr Construct:

Aradidopsis-etr mutant (SEQ ID NO: 15) was obtained by PCR from pMON11064 (FIG. 4). PCR reaction was set up using dsb 124 (SEQ ID: 13) and dsb 125 (SEQ ID NO: 14) primers.

dsb 124: 5' GCATGCCATGGAAGTCTGCAATTGTAT-TGAAC 3' with NcoI site and dsb 125: 5' CCGGAATTCT-TACATGCCCTCGTACAGTACC 3' with EcoRI site.

Figure 7:
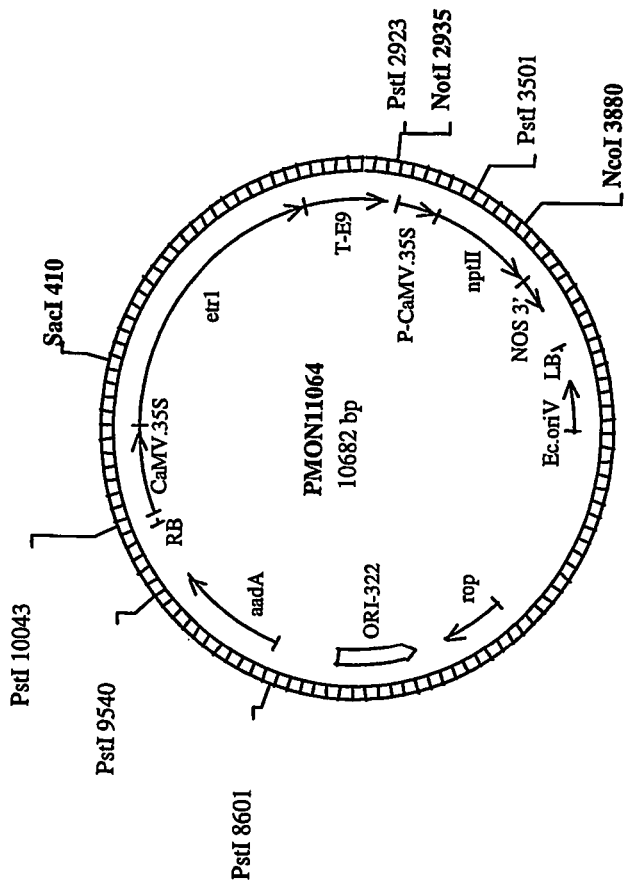
FIG. 7 shows a plasmid map of pMON11064.

PCR conditions were set up as follows: Template used was 1 ul of diluted (1:100) DNA from pMON11064 (FIG. 7). Buffer was added to 1×, 0.2 um dNIP, 1 ul of 10 uM dsb 124,dsb 125 primer each and Taq polymerase was added.

PCR conditions are as follows: 94° C. for 2 mins for one cycle, 94° C. for 30 sec, 55° C. for 30 sec, 68° C. for 2½ mins, this cycle is repeated 34 more times, One extension cycle at 72° C. for 10 mins and hold at 10° C. forever. Expected band size is about 2.2 kb.

PCR product's were then digested with the two enzymes Nco I and EcoRI and at the same time pMON 42502 also digested with NcoI and EcoRI. This would remove the GUS insert from pMON 42502 and it will be replaced with the PCR fragment created using dsb 124 and dsb 125. Both the digested reactions are run on a gel. Bands were cut out and gel purified as before.

A ligation reaction was set up using Rapid DNA Ligation Kit (cat # 1 635379) as follows: 10 μl of digested pMON54989 (FIG. 1), 6 μl of insert; A6 promoter was added to a ligation reaction which contains 10 μl of 2× ligation buffer and 1 μl of ligase, 5 units/μl. The reaction was ligated at RT for 15 minutes. 2 ul of this ligation reaction was transformed into 100 ul of Max Efficiency DH5αCompetent Cells, from Gibco-BRL, cat # 18258-012. The transformation mix was spread onto LB plates containing 100 μg/ml of ampicillin. Plates are incubated overnight at 37° C.

Figure 3:
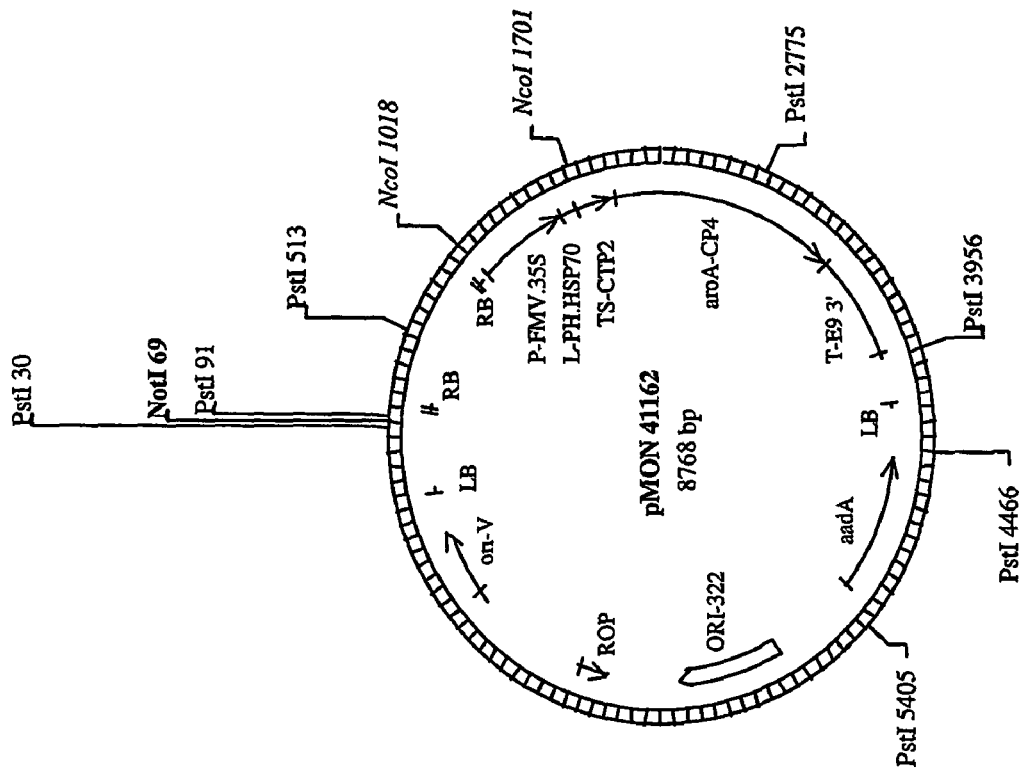
FIG. 3 shows a plasmid map of pMON41162.

A single colony was isolated and inoculated into 3 ml of LB containing 100 ug/ml ampicillin. Colonies were incubated at 37° C. in a shaking incubator. A miniprep was done on the colonies using Qiagen spin miniprep kit (250), cat # 27106 (Qiagen Inc. 28159 Avenue Stanford, Valencia, Calif. 91355). Instructions were followed according to the manufacturer's protocol. To confirm the presence of insert in the DNA, 5 ul of the minprep DNA was digested with EcoR1 and Nco1. The DNA prep that showed the 2.2 kb band indicates it had the insert in it. A large scale prep was prepared for the positive clone. This shuttle vector used is called pMON42504 (FIG. 3).

A large-scale prep was prepared for two of the above clones for pMON42504, using Qiagen Plasmid Midi kit (50), cat # 12144. This was digested with Not1 to obtain the region: P-A6-Ara-etr-NOS. This insert was inserted into a 2T vector, pMON 41162 at Not1 site. pMON41162 (FIG. 3) is the binary vector used for transformation.

DNA for pMON41162 had been previously digested with Not1 using Gibco-BRL enzyme Not1. After the digestion was completed, the 5' end was de-phosphorylated to prevent self-ligation. This reaction was done in the presence of 1× phosphatase buffer and 1 unit of Calf Intestinal Alkaline Phoshatase enzyme (BMB, cat # 18009-019). Manufacturer's instructions were followed.

Figure 8:
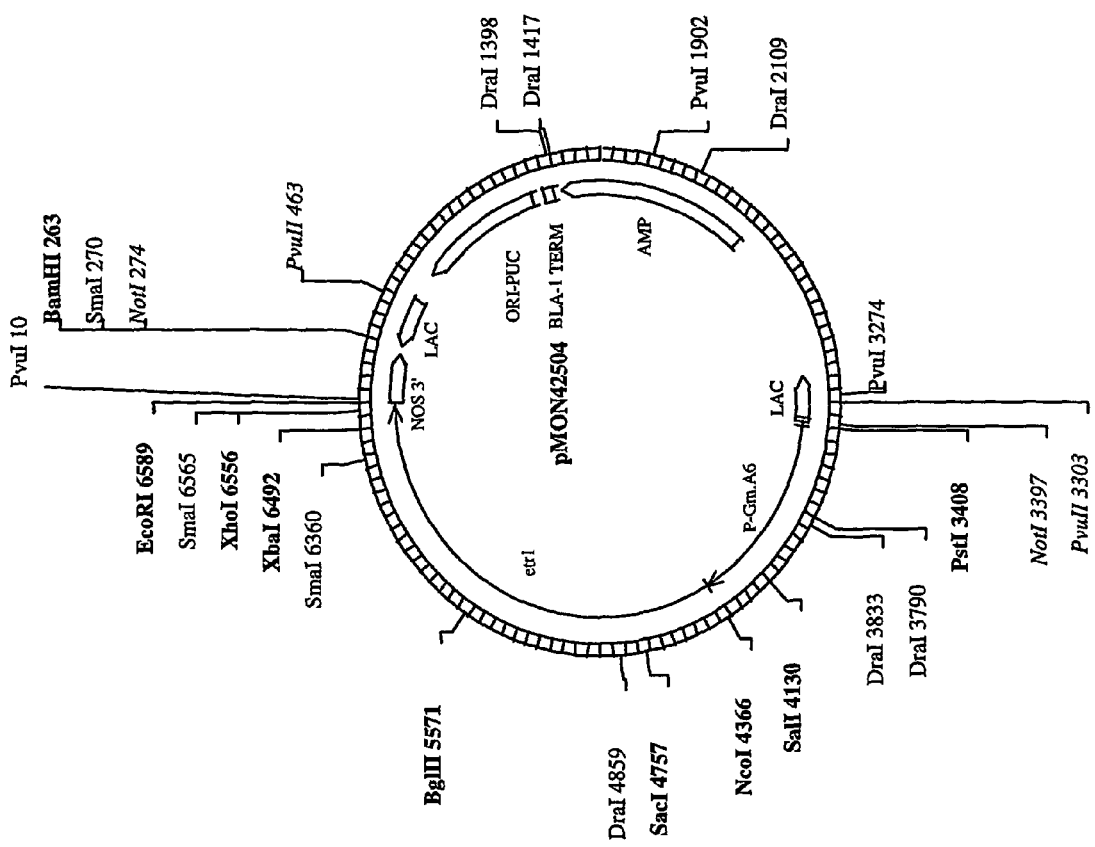
FIG. 8 shows a plasmid map of pMON42504.

DNA for pMON42504 (FIG. 8) was also digested with Not1, as above. After the digestion was complete, both reactions were run on an agarose gel. DNA was extracted from the gel for both pMON 42504 and pMON 41162. A ligation reaction was set up as follows: 2 ul of de-phosphorylated pMON41162, 5 ul of insert from pMON42502 was added to a ligation reaction which also contained 10 ul of 2× ligation buffer and 1 ul of ligase, 5 units/ul. The reaction is ligated at RT for 15 minutes. 2 ul of this ligation reaction is transformed into 100 ul of Max Efficiency DH5αCompetent Cells, from Gibco-BRL, cat # 18258-012. The transformation mix was spread onto LB plates containing 50 ug/ml of streptomycin. Plates are incubated overnight at 37° C.

Figure 9:
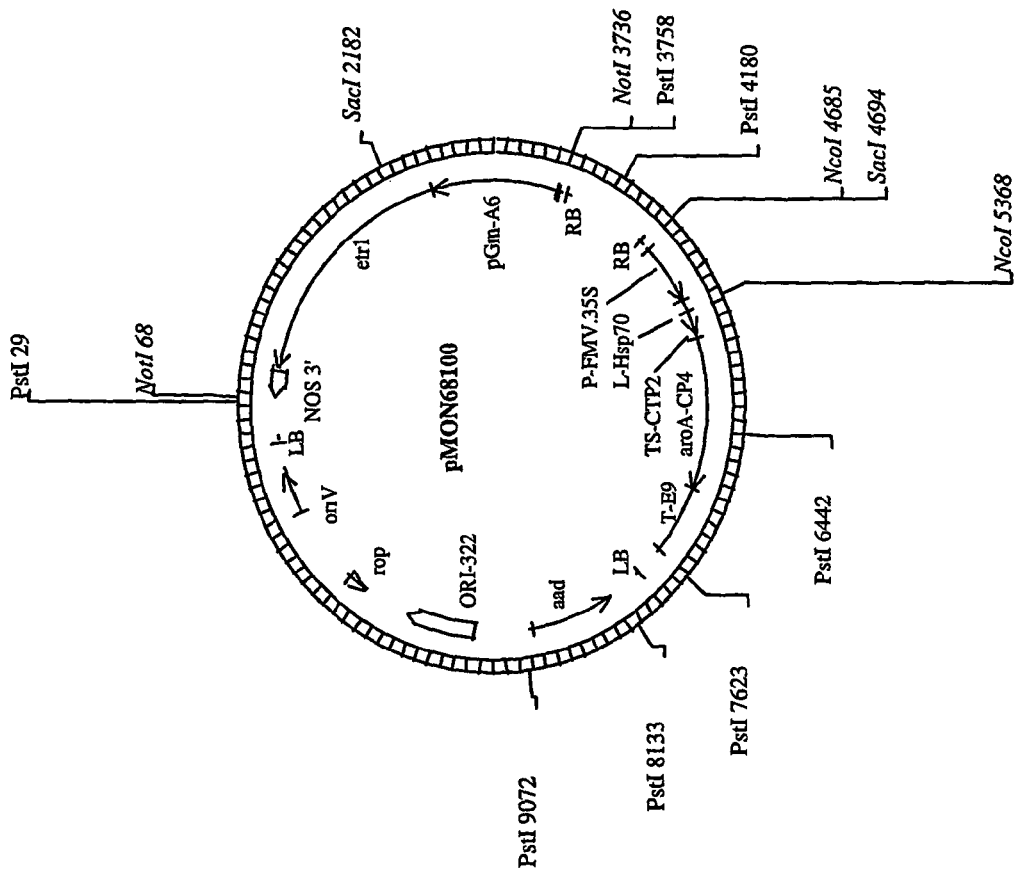
FIG. 9 shows a plasmid map of pMON68100.

A miniprep was done on the colonies using Qiagen spin miniprep kit (250), cat #27106 (Qiagen Inc. 28159 Avenue Stanford, Valencia, Calif. 91355). Instructions were followed according to the manufacturer's protocol. To confirm the presence of insert in the DNA, 5 ul of the minprep DNA was digested with Not1. The digested DNA prep that showed ~3 kb band indicates it has P-A6-Ara-etr-NOS insert in it. A large scale prep was prepared on two clones. The final vector was called pMON68100 (FIG. 9), using Qiagen Plasmid Midi kit (50), cat # 12144. The plasmid was checked with six different enzymes to determine the orientation of the P-A6-Ara-etr-NOS in pMON41162. An orientation where both the P-A6 and P-FMV.35S are located at the right border (RB) of the cassette was preferred and selected. The correct orientation was also confirmed by sequencing the junctions between the ligated portions. The vector created was called pMON68100 (FIG. 9). Transformation was done as in Example 2. One hundred and ten transformation (E9 terminator) positive plants were created.

Example 7

Greenhouse Test of pMON73967 Transgenic Plants of Event GM_A32054, Example Phenotypes.

R1 seeds obtained from a heterozygous soybean transformed with pMON73967 were sown in pots in a greenhouse using standard greenhouse practices (peat-based growth medium, supplemental lighting as needed for natural photoperiod, and pest control.). The peat-based potting mix was inoculated at planting with *Bradyrhizobium japonicum* to enable the soybeans to nodulate. Additional fertilization was supplied, as needed throughout the growing period.

The plants were exposed to short-day photoperiod to assure termination of vegetative growth and grown to maturity. These plants displayed a range of phenotypes.

RT-PCR was done to verify gene expression of IPT in GM_A32054 selection 64 leaf. RNA was extracted from fully expanded, leaf tissue of selection 64 and RT-PCR analysis was conducted to determine if the transcript for the IPT gene was being generated in the leaf. Control probes (A and B) were used to verify the detection endogenous transcripts. As seen in lanes 1 and 4 of FIG. 11, the transcript for IPT is not detectable in the A3244 (non-transformed plant) and is detectable in the leaf of selection 64. The expected fragment size generated from the IPT transcript is 311 base-pairs. This process utilized the Qiagen Rneasy™ RNA Mini Kit (Cat. No. 74904. Lot No. 4094516) to extract the RNA and the Invitrogen SuperScript™ One-Step RT-PCR with Paltinum® Taq (Cat No. 10928-034, Lot No. 1150422) to accomplish the RT-PCR. The probes used were internal to the IPT gene (GTCTCTTGGTCGGGTAACTT (Seq ID NO: 26) and GCTTCCAGTCCTTTCGCTTGA (SEQ ID NO: 27)).

After determining that these plants expressed IPT, further data was collected. Data collected at maturity from the plants described are displayed in FIG. 12. Across the population there was an increase in the mean and median number of nodes, branches, pods and seeds in the transgenics compared to the A3244 non-transformed background. These phenotypes could be indicative of plants with increased yield in a field test.

A field test of pMON73967 Transgenic Event GM_A32498 was also undertaken. Seed of soybeans transformed with pMON73967 were grown under field conditions in Illinois using standard agronomic practices. Phenotypic data on the segregating event GM_A32498 was collected at the R6 (fully podded) growth stage and is displayed in FIGS. 10 and 13. As can be seen, at this stage of growth, the transgenic plants displayed phenotypes with more main stem nodes and more pods at the plant apex.

The above results led to further testing in a growth chamber of plants transformed with pMON73967 (specifically event GM_A32498 lines 50 and 150). Seed from the progeny of field-grown GM_A32498 was sown in pots in a growth chamber under a 12 hour photoheriod, 50% relative humidity, 23 C day and 21 C night temperatures. The pots were inoculated with *Bradyrhizobium japonicum* and additional fertilization was supplied to meet minimum nutritional requirements. Phenotypic data was collected prior to maturity and is displayed in FIGS. 14, 15, and 16. The transgenic plants displayed an increase in nodes, branches, pods, and seed compared to the non-transgenic genetic background. HET1 and HOM1 are heterozygous and homozygous plants from the same parent. NEG plants are negative segregants from the same parents (which do not contain the transgene) and HOM2 plants are homozygous plants from second line derived from the GM_A32498 field material.

Example 8

Northern Blot Showing Expression of the Gene Downstream of the A6 Promoter in the Native Plant.

This developmental northern of soybean expression of the endogenous A6-linked gene presents results for the following tissues shown in Table 2 and FIG. 17.

TABLE 2

| Label | Tissue |
|---|---|
| 4d hypo | 4 day after germination hypocotyls |
| 4d cot | 4 day after germination cotyledon |
| 4d root | 4 day after germination root tissue |
| 7d root | 7 days after germination root tissue |
| 7d SAM | 7 days after germination shoot apical meristem |
| 7d cot + hypo | 7 days after germination cotyledon and hypocotyl combined |
| 7d leaf | 7 days after germination leaf tissue |
| V4 root | Root from plant at V4 stage |
| V4 internode | Internode from plant at V4 stage |
| V4 SAM | Shoot apical meristerm from plant at V4 stage |
| V4 leaf | Leaf tissue from plant at V4 stage |
| R3 Root | Root tissue from plant at R3 stage |
| R3 SAM | Shoot apical meristem from plant at R3 stage |
| R3 internode | Internode from plant at R3 stage |
| R3 AZ | Flower abscission zone from plant at R3 stage |
| R3 LAZ | Leaf abscission zone from plant at R3 stage |
| R3 Leaf | Leaf tissue from plant at R3 stage |
| R3 Flower | Flower tissue from plant at R3 stage |
| R5 Flower | Flower tissue from plant at R5 stage |
| R5 AZ | Flower abscission zone from plant at R5 stage |
| R5 pod | Pod tissue from plant at R5 stage |
| R5 podwall | Pod wall tissue from plant at R5 stage |
| R5 LAZ | Leaf abscission zone from plant at R5 stage |
| R5 root | Root tissue from plant at R5 stage |
| R5 leaf | Leaf tissue from plant at R5 stage |

Example 10

Creation of Further Constructs with the A6 Promoter Driving the Expression of IPT.

Figure 18:
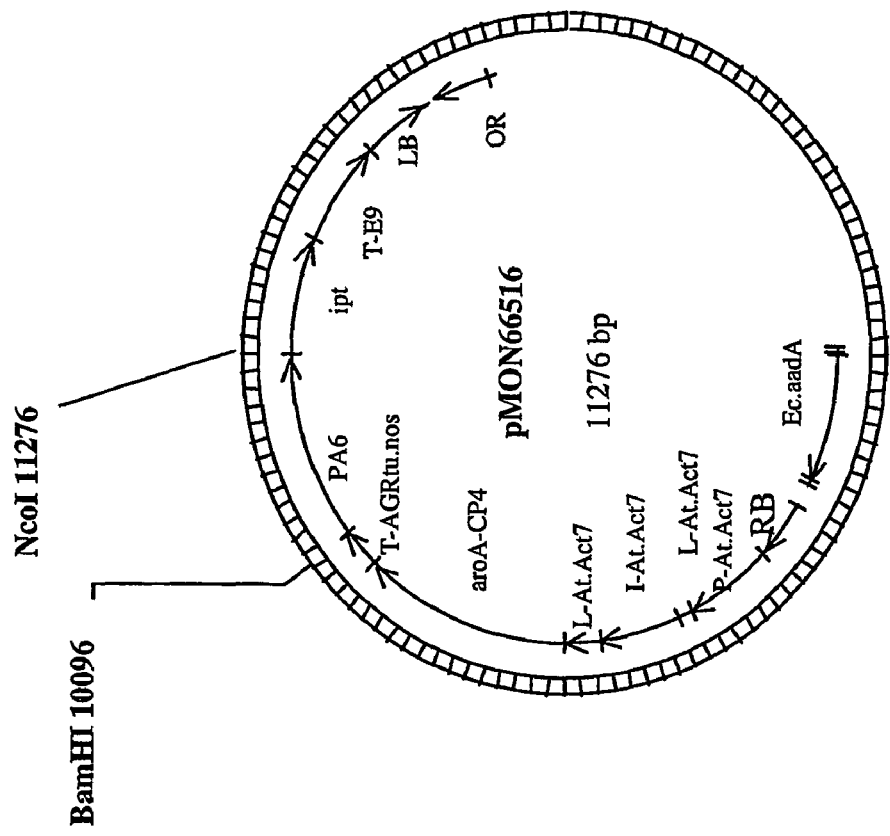
FIG. 18 shows pMON66516, a 1T vector with the A6 promoter driving the expression of IPT.

An IPT structural gene (SEQ ID NO:16) was linked to the A6 promoter in vector, PMON66516 (FIG. 18), which has been successfully transformed into soybean plants.

What is claimed is:

1. A recombinant nucleic acid molecule that has promoter activity in a plant cell and that comprises a sequence selected from the group consisting of:
   (a) the nucleic acid sequence of SEQ ID NO:1;
   (b) a fragment of SEQ ID NO:1 that directs transcription of an operably linked polynucleotide in at least one of the abscission zone(s), root, pod wall, apical meristem, or flower of a plant; and
   (c) a nucleic acid sequence comprising at least 95% identity to the polynucleotide sequence of SEQ ID NO:1, wherein said nucleic acid molecule is operably linked to a second DNA polynucleotide molecule.

2. The recombinant nucleic acid molecule of claim 1, wherein said promoter activity is enhanced in a tissue selected from the group consisting of pod abscission zone, leaf abscission zone, internode, leaf, root, pod wall, flower, and apical meristem.

3. An isolated DNA molecules that has promoter activity and that is isolated by amplification from soy genomic DNA using a first primer having SEQ ID NO:2 and a second primer having SEQ ID NO:3.

4. A recombinant DNA molecule comprising the isolated DNA molecule of claim 3, wherein said isolated DNA molecule is operably linked to a polynucleotide and is capable of initiating transcription of said polynucleotide in a plant cell.

5. The recombinant DNA molecule of claim 4, wherein said transcription is enhanced in a tissue selected from the group consisting of pod abscission zone, leaf abscission zone, internode, leaf, root, pod wall, flower, and apical meristem.

6. A transgenic plant having in its genome the recombinant DNA molecule of claim 4.

7. The transgenic plant of claim 6, wherein said transgenic plant is a crop plant selected from the group consisting of wheat, maize, rye, rice, oat, barley, turfgrass, sorghum, millet, sugarcane, tobacco, tomato, potato, soybean, cotton, canola, alfalfa, sunflower, and cotton.

8. The transgenic plant of claim 6, wherein said transgenic plant is a member of the *Glycine* genus, or a plant that can be bred with a plant that is a member of the *Glycine* genus.

9. A method of providing a transgenic crop plant having improved yield, comprising:
expressing in the transgenic crop plant the recombinant DNA molecule of claim 4;
wherein said expressing of said recombinant DNA molecule in said transgenic crop plant results in increased yield relative to yield in the absence of said expression.

10. The method of claim 9, wherein said polynucleotide encodes an isopentenyl transferase or an ethylene receptor.

11. The recombinant nucleic acid molecule of claim 1, wherein the nucleic acid molecule comprises the sequence of SEQ ID NO:1.

12. The recombinant nucleic acid molecule of claim 1, wherein the nucleic acid molecule comprises a fragment of SEQ ID NO:1 that directs transcription of an operably linked polynucleotide in at least one of the abscission zone(s), root, pod wall, apical meristem, or flower of a plant.

13. The recombinant nucleic acid molecule of claim 1, wherein the nucleic acid molecule comprises at least 95% identity to the polynucleotide sequence of SEQ ID NO:1.

14. The recombinant nucleic acid molecule of claim 1, wherein the nucleic acid molecule comprises at least 98% identity to the polynucleotide sequence of SEQ ID NO:1.

15. The recombinant nucleic acid molecule of claim 1, wherein the second DNA polynucleotide encodes an isopentenyl transferase or an ethylene receptor.

16. A transgenic plant transformed with the recombinant nucleic acid molecule of claim 1.

17. The transgenic plant of claim 16, wherein said transgenic plant is a plant selected from the group consisting of wheat, maize, rye, rice, oat, barley, turfgrass, sorghum, millet, sugarcane, tobacco, tomato, potato, soybean, cotton, canola, alfalfa, sunflower, and cotton.

18. The transgenic plant of claim 16, wherein said transgenic plant is a member of the *Glycine* genus, or a plant that can be bred with a plant that is a member of the *Glycine* genus.

19. The transgenic plant of claim 16, wherein the second DNA polynucleotide encodes an isopentenyl transferase or an ethylene receptor.

20. A method of expressing a second DNA polynucleotide molecule comprising introducing into a plant the nucleic acid molecule of claim 1.

21. The method of claim 20, wherein said second DNA polynucleotide molecule encodes an isopentenyl transferase or an ethylene receptor.

22. A transgenic seed transformed with the recombinant nucleic acid molecule of claim 1.

23. The transgenic seed of claim 22, wherein the nucleic acid molecule comprises the sequence of SEQ ID NO:1.

24. The transgenic seed of claim 22, wherein the nucleic acid molecule comprises a fragment of SEQ ID NO:1 that directs transcription of an operably linked polynucleotide in at least one of the abscission zone(s), root, pod wall, apical meristem, or flower of a plant.

25. The transgenic seed of claim 22, wherein the nucleic acid molecule comprises at least 95% identity to the polynucleotide sequence of SEQ ID NO:1.

26. The transgenic seed of claim 22, wherein the nucleic acid molecule comprises at least 98% identity to the polynucleotide sequence of SEQ ID NO:1.

27. The transgenic plant of claim 16, wherein the nucleic acid molecule comprises the sequence of SEQ ID NO:1.

28. The transgenic plant of claim 16, wherein the nucleic acid molecule comprises a fragment of SEQ ID NO:1 hat directs transcription of an operably linked polynucleotide in at least one of the abscission zone(s), root, pod wall, apical meristem, or flower of a plant.

29. The transgenic plant of claim 16, wherein the nucleic acid molecule comprises at least 95% identity to the polynucleotide sequence of SEQ ID NO:1.

30. The transgenic plant of claim 16, wherein the nucleic acid molecule comprises at least 98% identity to the polynucleotide sequence of SEQ ID NO:1.

* * * * *

UNITED STATES PATENT AND TRADEMARK OFFICE
CERTIFICATE OF CORRECTION

| | | |
|---|---|---|
| PATENT NO. | : 7,799,970 B2 | |
| APPLICATION NO. | : 10/545472 | |
| DATED | : September 21, 2010 | |
| INVENTOR(S) | : Bhat et al. | |

It is certified that error appears in the above-identified patent and that said Letters Patent is hereby corrected as shown below:

In claim 28, column 50, line 28, delete "hat" and insert --that--.

Signed and Sealed this
Twenty-sixth Day of April, 2011

David J. Kappos
*Director of the United States Patent and Trademark Office*

```
                        SEQUENCE LISTING

<160> NUMBER OF SEQ ID NOS: 24

<210> SEQ ID NO 1
<211> LENGTH: 1160
<212> TYPE: DNA
<213> ORGANISM: Glycine Max

<400> SEQUENCE: 1
tcacaagaca aaccttaaac ataccatacc atccttttat ctatctctac ttcaaaatca     60
atttttgcaa cattcactca atggtgcact taattaacaa accctcatcc atatacacat    120
atttagagat caacaatatg attatctatc aaaaatacac aaaatcagtg tgtgtttggg    180
taggcgttga caaaaattag ttttgaatga aattgatttt ataaattttt ttttgttaaa    240
attgattttg aagtaatatt atttatgttt ggatgtttta ttaaaaaatt aagttatgaa    300
taaaatgaag tacataattt tggaccaaaa attattcaaa attatttcaa cccaaaatta    360
attctgtatc caaagtcaat tttaaatttt tctttgatgt gaaactaaac atgtaaaaat    420
gtatttaaat taaaattaat tttagactta taattaattc tctgtggtca atccaaatac    480
acactcacac ttagaatgta tgaaatttca attttaact ttctcatcta tgagctgttc    540
ctattcctcc ttcccctcct atgccctcac tagggagcca gccagccata ttccaaaagc    600
ccttattatc acacatgggt ccctccatag tcaaaataaa aataatatca tgatcactgt    660
ttggccataa agagctatac gacacacatg gacacagtag tacactgccc aaccaatcac    720
acgtcgacag cacaccgttc ccaaactact tcacctttcc caaaccagaa accaaaacca    780
cttgtcatca aaccctgcc cagatagttt ttctccattt caatatttta cttcaccttt    840
tgaggctttg tgggtactac aaaacataac acaattgaac tcactgtgct ttcccatgac    900
acacatctat acttgtccag aagaagaaag atccatgaac taacattccc acacgctcgc    960
ttcaccatat ttgccaccct tttaaccctc acttcttggg tttattttgc tcctttttt    1020 tttccttgtt tggggtttgc attttttcctg gttgaaaaag ggaagaactt gaactaattg   1080
gttaagttac ctatctatct atctatctaa ggtataatat tttatatcag ttattaaagg   1140
aaagaaagaa agaaacgaag                                               1160
```

```
<210> SEQ ID NO 2
<211> LENGTH: 39
<212> TYPE: DNA
<213> ORGANISM: Artificial Sequence
<220> FEATURE:
<223> OTHER INFORMATION: Full Length artificially created primer for DNA
      amplification
<220> FEATURE:
<221> NAME/KEY: NcoI_site
<222> LOCATION: (1)..(6)
<223> OTHER INFORMATION: Glycine max with NcoI site on 5' end

<400> SEQUENCE: 2
ccatggcttc gtttctttct ttctttcctt taataactg                              39

<210> SEQ ID NO 3
<211> LENGTH: 36
<212> TYPE: DNA
<213> ORGANISM: Artificial Sequence
<220> FEATURE:
<223> OTHER INFORMATION: Full Length artificially created primer for DNA
      amplification
<220> FEATURE:
<221> NAME/KEY: PstI_site
<222> LOCATION: (1)..(6)
<223> OTHER INFORMATION: Glycine max with PstI site at 5' end

<400> SEQUENCE: 3
ctgcagtcac aagacaaacc ttaaacatac catacc                                 36

<210> SEQ ID NO 4
<211> LENGTH: 18
<212> TYPE: DNA
<213> ORGANISM: Artificial Sequence
<220> FEATURE:
<223> OTHER INFORMATION: Full Length artificially created primer for DNA
      amplification
<220> FEATURE:
<221> NAME/KEY: M13F
<222> LOCATION: (1)..(18)
<223> OTHER INFORMATION: Commercially available sequencing primer

<400> SEQUENCE: 4
ggttttccca gtcacgac                                                     18

<210> SEQ ID NO 5
<211> LENGTH: 20
<212> TYPE: DNA
<213> ORGANISM: Artificial Sequence
<220> FEATURE:
<223> OTHER INFORMATION: Full Length artificially created primer for DNA
      amplification
<220> FEATURE:
<221> NAME/KEY: M13R
<222> LOCATION: (1)..(20)
<223> OTHER INFORMATION: Commercially available sequencing primer

<400> SEQUENCE: 5
cacaggaaac agctatgacc                                                   20

<210> SEQ ID NO 6
<211> LENGTH: 23
<212> TYPE: DNA
<213> ORGANISM: Artificial Sequence
<220> FEATURE:
<223> OTHER INFORMATION: Full Length artificially created primer for DNA
      amplification
<220> FEATURE:
<221> NAME/KEY: Primer
<222> LOCATION: (1)..(23)
```

```
<223> OTHER INFORMATION: Artificial primer specifically created for DNA
      amplification, hybridizes to the A6 promoter (SEQ ID NO: 1)

<400> SEQUENCE: 6
ccctgcccag atagttttc tcc                                                23

<210> SEQ ID NO 7
<211> LENGTH: 20
<212> TYPE: DNA
<213> ORGANISM: Artificial Sequence
<220> FEATURE:
<223> OTHER INFORMATION: Full Length artificially created primer for DNA
      amplification
<220> FEATURE:
<221> NAME/KEY: Primer
<222> LOCATION: (1)..(20)
<223> OTHER INFORMATION: Artificial DNA amplification primer, hybridizes
      to GUS

<400> SEQUENCE: 7
caattgcccg gctttcttgt                                                   20

<210> SEQ ID NO 8
<211> LENGTH: 20
<212> TYPE: DNA
<213> ORGANISM: Artificial Sequence
<220> FEATURE:
<223> OTHER INFORMATION: Full Length artificially created primer for DNA
      amplification
<220> FEATURE:
<221> NAME/KEY: Primer
<222> LOCATION: (1)..(20)
<223> OTHER INFORMATION: Artificial DNA amplification primer, hybridizes
      to CP4
<220> FEATURE:
<221> NAME/KEY: Primer
<222> LOCATION: (1)..(20)
<223> OTHER INFORMATION: Artificial DNA amplification primer, hybridizes
      to FMV

<400> SEQUENCE: 8
tgtcagcttt caaactcttt                                                   20

<210> SEQ ID NO 9
<211> LENGTH: 24
<212> TYPE: DNA
<213> ORGANISM: Artificial Sequence
<220> FEATURE:
<223> OTHER INFORMATION: Full Length artificially created primer for DNA
      amplification
<220> FEATURE:
<221> NAME/KEY: Primer
<222> LOCATION: (1)..(24)
<223> OTHER INFORMATION: Hybridizes to CP4, DNA amplification primer

<400> SEQUENCE: 9
ggagagttcg atcttagctc caag                                              24

<210> SEQ ID NO 10
<211> LENGTH: 20
<212> TYPE: DNA
<213> ORGANISM: Artificial Sequence
<220> FEATURE:
<223> OTHER INFORMATION: Full Length artificially created primer for DNA
      amplification

<400> SEQUENCE: 10
tgttcggcgt ggtgtagagc                                                   20
```

-continued

<210> SEQ ID NO 11
<211> LENGTH: 24
<212> TYPE: DNA
<213> ORGANISM: Artificial Sequence
<220> FEATURE:
<223> OTHER INFORMATION: Full Length artificially created primer for DNA
      amplification

<400> SEQUENCE: 11
cagcattcca gattgggttc aatc                                           24

<210> SEQ ID NO 12
<211> LENGTH: 21
<212> TYPE: DNA
<213> ORGANISM: Artificial Sequence
<220> FEATURE:
<223> OTHER INFORMATION: Full Length artificially created primer for DNA
      amplification
<220> FEATURE:
<221> NAME/KEY: Primer
<222> LOCATION: (1)..(21)
<223> OTHER INFORMATION: Full Length artificially created primer for DNA
      amplification

<400> SEQUENCE: 12
cacgcaaggt aactggaaga c                                              21

<210> SEQ ID NO 13
<211> LENGTH: 32
<212> TYPE: DNA
<213> ORGANISM: Artificial
<220> FEATURE:
<223> OTHER INFORMATION: Arabidopsis Etr-1 primer with NcoI site

<400> SEQUENCE: 13
gcatgccatg gaagtctgca attgtattga ac                                  32

<210> SEQ ID NO 14
<211> LENGTH: 31
<212> TYPE: DNA
<213> ORGANISM: Artificial
<220> FEATURE:
<223> OTHER INFORMATION: Arabidopsis Etr-1 primer with EcoRI site

<400> SEQUENCE: 14
ccggaattct tacatgcccct cgtacagtac c                                  31

<210> SEQ ID NO 15
<211> LENGTH: 2217
<212> TYPE: DNA
<213> ORGANISM: Arabidopsis thaliana
<220> FEATURE:
<221> NAME/KEY: mutation
<222> LOCATION: (193)..(195)
<223> OTHER INFORMATION: aa65 encodes a mutant Cys to Tyr

<400> SEQUENCE: 15
atggaagtct gcaattgtat tgaaccgcaa tggccagcgg atgaattgtt aatgaaatac     60
caatacatct ccgatttctt cattgcgatt gcgtattttt cgattcctct tgagttgatt    120
tactttgtga agaaatcagc cgtgtttccg tatagatggg tacttgttca gtttggtgct    180
tttatcgttc tttgtggagc aactcatctt attaacttat ggactttcac tacgcattcg    240
agaaccgtgg cgcttgtgat gactaccgcg aaggtgttaa ccgctgttgt ctcgtgtgct    300
actgcgttga tgcttgttca tattattcct gatcttttga gtgttaagac tcggagcttt    360
ttcttgaaaa ataaagctgc tgagctcgat agagaaatgg gattgattcg aactcaggaa    420

```
gaaaccggaa ggcatgtgag aatgttgact catgagatta gaagcactt  agatagacat    480 actattttaa agactacact tgttgagctt ggtaggacat tagctttgga ggagtgtgca    540
ttgtggatgc ctactagaac tgggttagag ctacagcttt cttatacact tcgtcatcaa    600
catcccgtgg agtatacggt tcctattcaa ttaccgtga  ttaaccaagt gtttggtact    660
agtagggctg taaaaatatc tcctaattct cctgtggcta ggttgagacc tgtttctggg    720
aaatatatgc taggggaggt ggtcgctgtg agggttccgc ttctccacct ttctaatttt    780
cagattaatg actggcctga gctttcaaca aagagatatg ctttgatggt tttgatgctt    840
ccttcagata gtgcaaggca atggcatgtc catgagttgg aactcgttga agtcgtcgct    900
gatcaggtgg ctgtagctct ctcacatgct gcgatcctag aagagtcgat gcagctagg     960 gaccttctca tggagcagaa tgttgctctt gatctagcta gacgagaagc agaaacagca   1020
atccgtgccc gcaatgattt cctagcggtt atgaaccatg aaatgcgaac accgatgcat   1080
gcgattattg cactctcttc cttactccaa gaaacggaac taacccctga acaaagactg   1140
atggtggaaa caatacttaa aagtagtaac cttttggcaa cttttgatga atgatgtctta  1200 gatctttcaa ggttagaaga tggaagtctt caacttgaac ttgggacatt caatcttcat   1260
acattattta gagaggtcct caatctgata aagcctatag cggttgttaa gaaattaccc   1320
atcacactaa atcttgcacc agatttgcca gaatttgttg ttggggatga gaaacggcta   1380
atgcagataa tattaaatat agttggtaat gctgtgaaat tctccaaaca aggtagtatc   1440
tccgtaaccg ctcttgtcac caagtcgac  acacgagctg ctgactttt  tgtcgtgcca   1500 actgggagtc atttctactt gagagtgaag gtaaaagact ctggagcagg aataaatcct   1560
caagacattc caaagatttt cactaaattt gctcaaacac aatctttagc gacgagaagc   1620
tcgggtggta gtgggcttgg cctcgccatc tccaagaggt ttgtgaatct gatggagggt   1680
aacatttgga ttgagagcga tggtcttgga aaaggatgca cggctatctt tgatgttaaa   1740
cttgggatct cagaacgttc aaacgaatct aaacagtcgg gcataccgaa agttccagcc   1800
attccccgac attcaaattt cactggactt aaggttcttg tcatggatga aacggggta    1860 agtagaatgg tgacgaaggg acttcttgta caccttgggt gcgaagtgac cacggtgagt   1920
tcaaacgagg agtgtctccg agttgtgtcc catgagcaca aagtggtctt catgacgtg    1980 tgcatgcccg gggtcgaaaa ctaccaaatc gctctccgta ttcacgagaa attcacaaaa   2040
caacgccacc aacggccact acttgtggca ctcagtggta acactgacaa atccacaaaa   2100
gagaaatgca tgagctttgg tctagacggt gtgttgctca aacccgtatc actagacaac   2160
ataagagatg ttctgtctga tcttctcgag ccccgggtac tgtacgaggg catgtaa      2217

<210> SEQ ID NO 16
<211> LENGTH: 744
<212> TYPE: DNA
<213> ORGANISM: Agrobacterium tumefaciens

<400> SEQUENCE: 16
catggaccct gcatctaatt ttcggtccaa cttgcacagg aaagacgacg accgcgatag     60
ctcttgccca gcagacaggg cttccagtcc tttcgcttga tcgggtccaa tgctgtcctc    120
aactatcaac cggaagcgga cgaccaacag tggaagaact gaaaggaacg acgcgtctct    180
accttgatga tcggcctctg gtgggggta  tcatcgcagc caagcaagct catcataggc    240
tgatcgagga ggtgtataat catgaggcca acggcgggct tattcttgag ggaggatcca    300
```

```
cctcgttgct caactgcatg gcgcgaaaca gctattggag tgcagatttt cgttggcata    360
ttattcgcca caagttaccc gaccaagaga ccttcatgaa agcggccaag gccagagtta    420
agcagatgtt gcaccccgct gcaggccatt ctattattca agagttggtt tatctttgga    480
atgaacctcg gctgaggccc attctgaaag agatcgatgg atatcgatat gccatgttgt    540
ttgctagcca gaaccagatc acggcagata tgctattgca gcttgacgca aatatggaag    600
gtaagttgat taatgggatc gctcaggagt atttcatcca tgcgcgccaa caggaacaga    660
aattccccca agttaacgca gccgctttcg acggattcga aggtcatccg ttcggaatgt    720
attaggttac gccagccctg agct                                          744
```

```
<210> SEQ ID NO 17
<211> LENGTH: 723
<212> TYPE: DNA
<213> ORGANISM: Agrobacterium tumefaciens
<220> FEATURE:
<221> NAME/KEY: CDS
<222> LOCATION: (1)..(723)
<223> OTHER INFORMATION:

<400> SEQUENCE: 17
```

```
atg gat ctg cgt cta att ttc ggt cca act tgc aca gga aag acg tcg    48
Met Asp Leu Arg Leu Ile Phe Gly Pro Thr Cys Thr Gly Lys Thr Ser
1               5                  10                  15 acc gcg gta gct ctt gcc cag cag act ggg ctt cca gtc ctt tcg ctc    96
Thr Ala Val Ala Leu Ala Gln Gln Thr Gly Leu Pro Val Leu Ser Leu
                20                  25                  30 gat cgg gtc caa tgt tgt cct cag ctg tca acc gga agc gga cga cca   144
Asp Arg Val Gln Cys Cys Pro Gln Leu Ser Thr Gly Ser Gly Arg Pro
            35                  40                  45 aca gtg gaa gaa ctg aaa gga acg agc cgt cta tac ctt gat gat cgg   192
Thr Val Glu Glu Leu Lys Gly Thr Ser Arg Leu Tyr Leu Asp Asp Arg
        50                  55                  60 cct ctg gtg aag ggt atc atc gca gcc aag caa gct cat gaa agg ctg   240
Pro Leu Val Lys Gly Ile Ile Ala Ala Lys Gln Ala His Glu Arg Leu
65                  70                  75                  80 atg ggg ggt gtg tat aat tat gag gcc cac ggc ggg ctt att ctt gag   288
Met Gly Gly Val Tyr Asn Tyr Glu Ala His Gly Gly Leu Ile Leu Glu
                85                  90                  95 gga gga tct atc tcg ttg ctc aag tgc atg gcg caa agc agt tat tgg   336
Gly Gly Ser Ile Ser Leu Leu Lys Cys Met Ala Gln Ser Ser Tyr Trp
            100                 105                 110 agt gcg gat ttt cgt tgg cat att att cgc cac gag tta gca gac gaa   384
Ser Ala Asp Phe Arg Trp His Ile Ile Arg His Glu Leu Ala Asp Glu
        115                 120                 125 gag acc ttc atg aac gtg gcc aag gcc aga gtt aag cag atg tta cgc   432
Glu Thr Phe Met Asn Val Ala Lys Ala Arg Val Lys Gln Met Leu Arg
    130                 135                 140 cct gct gca ggc ctt tct att atc caa gag ttg gtt gat ctt tgg aaa   480
Pro Ala Ala Gly Leu Ser Ile Ile Gln Glu Leu Val Asp Leu Trp Lys
145                 150                 155                 160 gag cct cgg ctg agg ccc ata ctg aaa gag atc gat gga tat cga tat   528
Glu Pro Arg Leu Arg Pro Ile Leu Lys Glu Ile Asp Gly Tyr Arg Tyr
                165                 170                 175 gcc atg ttg ttt gct agc cag aac cag atc aca tcc gat atg cta ttg   576
Ala Met Leu Phe Ala Ser Gln Asn Gln Ile Thr Ser Asp Met Leu Leu
            180                 185                 190 cag ctt gac gca gat atg gag gat aag ttg att cat ggg atc gct cag   624
Gln Leu Asp Ala Asp Met Glu Asp Lys Leu Ile His Gly Ile Ala Gln
        195                 200                 205
```

```
gag tat ctc atc cat gca cgc cga caa gaa cag aaa ttc cct cga gtt    672
Glu Tyr Leu Ile His Ala Arg Arg Gln Glu Gln Lys Phe Pro Arg Val
    210                 215                 220 aac gca gcc gct tac gac gga ttc gaa ggt cat cca ttc gga atg tat    720
Asn Ala Ala Ala Tyr Asp Gly Phe Glu Gly His Pro Phe Gly Met Tyr
225                 230                 235                 240 tag                                                                723

<210> SEQ ID NO 18
<211> LENGTH: 240
<212> TYPE: PRT
<213> ORGANISM: Agrobacterium tumefaciens

<400> SEQUENCE: 18

Met Asp Leu Arg Leu Ile Phe Gly Pro Thr Cys Thr Gly Lys Thr Ser
1               5                   10                  15

Thr Ala Val Ala Leu Ala Gln Gln Thr Gly Leu Pro Val Leu Ser Leu
            20                  25                  30

Asp Arg Val Gln Cys Cys Pro Gln Leu Ser Thr Gly Ser Gly Arg Pro
        35                  40                  45

Thr Val Glu Glu Leu Lys Gly Thr Ser Arg Leu Tyr Leu Asp Asp Arg
    50                  55                  60

Pro Leu Val Lys Gly Ile Ala Ala Lys Gln Ala His Glu Arg Leu
65                  70                  75                  80

Met Gly Gly Val Tyr Asn Tyr Glu Ala His Gly Gly Leu Ile Leu Glu
                85                  90                  95

Gly Gly Ser Ile Ser Leu Leu Lys Cys Met Ala Gln Ser Ser Tyr Trp
            100                 105                 110

Ser Ala Asp Phe Arg Trp His Ile Ile Arg His Glu Leu Ala Asp Glu
        115                 120                 125

Glu Thr Phe Met Asn Val Ala Lys Ala Arg Val Lys Gln Met Leu Arg
    130                 135                 140

Pro Ala Ala Gly Leu Ser Ile Ile Gln Glu Leu Val Asp Leu Trp Lys
145                 150                 155                 160

Glu Pro Arg Leu Arg Pro Ile Leu Lys Glu Ile Asp Gly Tyr Arg Tyr
                165                 170                 175

Ala Met Leu Phe Ala Ser Gln Asn Gln Ile Thr Ser Asp Met Leu Leu
            180                 185                 190

Gln Leu Asp Ala Asp Met Glu Asp Lys Leu Ile His Gly Ile Ala Gln
        195                 200                 205

Glu Tyr Leu Ile His Ala Arg Arg Gln Glu Gln Lys Phe Pro Arg Val
    210                 215                 220

Asn Ala Ala Ala Tyr Asp Gly Phe Glu Gly His Pro Phe Gly Met Tyr
225                 230                 235                 240

<210> SEQ ID NO 19
<211> LENGTH: 723
<212> TYPE: DNA
<213> ORGANISM: Agrobacterium vitis
<220> FEATURE:
<221> NAME/KEY: CDS
<222> LOCATION: (1)..(723)
<223> OTHER INFORMATION:

<400> SEQUENCE: 19 atg gat ctg cgt cta att ttc ggt cca act tgc aca gga aag acg tcg    48
Met Asp Leu Arg Leu Ile Phe Gly Pro Thr Cys Thr Gly Lys Thr Ser
1               5                   10                  15
```

| | |
|---|---|
| acg gcg ata gct ctt gcc cag cag act ggg ctt cca gtc ctt tcg ctc<br>Thr Ala Ile Ala Leu Ala Gln Gln Thr Gly Leu Pro Val Leu Ser Leu<br>20 25 30 | 96 |
| gat cgg gtc caa tgc tgt cct cag ctg tca acc gga agc gga cga cca<br>Asp Arg Val Gln Cys Cys Pro Gln Leu Ser Thr Gly Ser Gly Arg Pro<br>35 40 45 | 144 |
| aca gtg gaa gaa ctg aaa gga acg acc cgt ctg tac ctt gat gat cgg<br>Thr Val Glu Glu Leu Lys Gly Thr Thr Arg Leu Tyr Leu Asp Asp Arg<br>50 55 60 | 192 |
| ccc ctg gtg aag ggt atc atc gca gcc gag caa gct cat gag agg ctg<br>Pro Leu Val Lys Gly Ile Ile Ala Ala Glu Gln Ala His Glu Arg Leu<br>65 70 75 80 | 240 |
| atc gcg gag gtg tat aat tat gag gcc cac ggc gga ctt att ctt gag<br>Ile Ala Glu Val Tyr Asn Tyr Glu Ala His Gly Gly Leu Ile Leu Glu<br>85 90 95 | 288 |
| gga gga tct atc tcg ttg ctc aag tgc atg gcg caa agc ggt tat tgg<br>Gly Gly Ser Ile Ser Leu Leu Lys Cys Met Ala Gln Ser Gly Tyr Trp<br>100 105 110 | 336 |
| agc gcc gat ttt cgt tgg cat att att cgc cac aag tta gca gac gag<br>Ser Ala Asp Phe Arg Trp His Ile Ile Arg His Lys Leu Ala Asp Glu<br>115 120 125 | 384 |
| gag acc ttc atg aaa gcg gcc aag gcc aga gtt aag cag atg ttg tgc<br>Glu Thr Phe Met Lys Ala Ala Lys Ala Arg Val Lys Gln Met Leu Cys<br>130 135 140 | 432 |
| ccc gct ata ggc cca tct ctt att caa gag ttg gtt tat ctt tgg aat<br>Pro Ala Ile Gly Pro Ser Leu Ile Gln Glu Leu Val Tyr Leu Trp Asn<br>145 150 155 160 | 480 |
| gag cct cgg ctg agg ccc ata ctg aaa gag atc gat gga tat cga tat<br>Glu Pro Arg Leu Arg Pro Ile Leu Lys Glu Ile Asp Gly Tyr Arg Tyr<br>165 170 175 | 528 |
| gcc atg ttg ttt gct agc cag aat cgg atc acg ccc gat atg cta ttg<br>Ala Met Leu Phe Ala Ser Gln Asn Arg Ile Thr Pro Asp Met Leu Leu<br>180 185 190 | 576 |
| cag ctt gac gca gat atg gag ggt aag ttg att cat ggg atc gct cag<br>Gln Leu Asp Ala Asp Met Glu Gly Lys Leu Ile His Gly Ile Ala Gln<br>195 200 205 | 624 |
| gag tat ctc atc cat gcg cgt cgg cag gaa cac gaa ttc ccg ccg gtg<br>Glu Tyr Leu Ile His Ala Arg Arg Gln Glu His Glu Phe Pro Pro Val<br>210 215 220 | 672 |
| agc gcg gca gct ttc gaa gga ttt gaa ggc cca cca ttc gga gcg tac<br>Ser Ala Ala Ala Phe Glu Gly Phe Glu Gly Pro Pro Phe Gly Ala Tyr<br>225 230 235 240 | 720 |
| tag | 723 |

<210> SEQ ID NO 20
<211> LENGTH: 240
<212> TYPE: PRT
<213> ORGANISM: Agrobacterium vitis

<400> SEQUENCE: 20

Met Asp Leu Arg Leu Ile Phe Gly Pro Thr Cys Thr Gly Lys Thr Ser
1               5                   10                  15

Thr Ala Ile Ala Leu Ala Gln Gln Thr Gly Leu Pro Val Leu Ser Leu
                20                  25                  30

Asp Arg Val Gln Cys Cys Pro Gln Leu Ser Thr Gly Ser Gly Arg Pro
            35                  40                  45

Thr Val Glu Glu Leu Lys Gly Thr Thr Arg Leu Tyr Leu Asp Asp Arg
        50                  55                  60

```
Pro Leu Val Lys Gly Ile Ile Ala Ala Glu Gln Ala His Glu Arg Leu
 65                  70                  75                  80

Ile Ala Glu Val Tyr Asn Tyr Glu Ala His Gly Gly Leu Ile Leu Glu
                 85                  90                  95

Gly Gly Ser Ile Ser Leu Leu Lys Cys Met Ala Gln Ser Gly Tyr Trp
            100                 105                 110

Ser Ala Asp Phe Arg Trp His Ile Ile Arg His Lys Leu Ala Asp Glu
        115                 120                 125

Glu Thr Phe Met Lys Ala Ala Lys Ala Arg Val Lys Gln Met Leu Cys
    130                 135                 140

Pro Ala Ile Gly Pro Ser Leu Ile Gln Glu Leu Val Tyr Leu Trp Asn
145                 150                 155                 160

Glu Pro Arg Leu Arg Pro Ile Leu Lys Glu Ile Asp Gly Tyr Arg Tyr
                165                 170                 175

Ala Met Leu Phe Ala Ser Gln Asn Arg Ile Thr Pro Asp Met Leu Leu
            180                 185                 190

Gln Leu Asp Ala Asp Met Glu Gly Lys Leu Ile His Gly Ile Ala Gln
        195                 200                 205

Glu Tyr Leu Ile His Ala Arg Arg Gln Glu His Glu Phe Pro Pro Val
    210                 215                 220

Ser Ala Ala Ala Phe Glu Gly Phe Glu Gly Pro Pro Phe Gly Ala Tyr
225                 230                 235                 240

<210> SEQ ID NO 21
<211> LENGTH: 723
<212> TYPE: DNA
<213> ORGANISM: Agrobacterium vitis
<220> FEATURE:
<221> NAME/KEY: CDS
<222> LOCATION: (1)..(723)
<223> OTHER INFORMATION:
<300> PUBLICATION INFORMATION:
<308> DATABASE ACCESSION NUMBER: U83986
<309> DATABASE ENTRY DATE: 1997-01-07

<400> SEQUENCE: 21 atg gat ctg cgt cta att ttc ggt cca act tgc aca gga aag acg tcg      48
Met Asp Leu Arg Leu Ile Phe Gly Pro Thr Cys Thr Gly Lys Thr Ser
  1               5                  10                  15 acc gcg ata cgt ctt gcc cag cag act ggc ctt cca gtc ctt tcg ctc      96
Thr Ala Ile Arg Leu Ala Gln Gln Thr Gly Leu Pro Val Leu Ser Leu
             20                  25                  30 gat cgg gtc caa tgc tgt cct caa ctg tca acc gga agc gga cga cca     144
Asp Arg Val Gln Cys Cys Pro Gln Leu Ser Thr Gly Ser Gly Arg Pro
         35                  40                  45 aca gtg gaa gaa ctg aaa gga acg acc cgt cta tac ctt gaa gat cgg     192
Thr Val Glu Glu Leu Lys Gly Thr Thr Arg Leu Tyr Leu Glu Asp Arg
     50                  55                  60 cct ctg gtg aag ggt atc atc gca gcc aag caa gct cac gaa agg ctg     240
Pro Leu Val Lys Gly Ile Ile Ala Ala Lys Gln Ala His Glu Arg Leu
 65                  70                  75                  80 atc ggg gaa gtg tac aat tat gag gcc cac ggc ggg ctt att ctt gag     288
Ile Gly Glu Val Tyr Asn Tyr Glu Ala His Gly Gly Leu Ile Leu Glu
                 85                  90                  95 gga gga tct atc tcg ttg ctc agg tgc atg gcg caa agc agt tat tgg     336
Gly Gly Ser Ile Ser Leu Leu Arg Cys Met Ala Gln Ser Ser Tyr Trp
            100                 105                 110 agt acc gat ttt cgt tgg cat att att cgc cac aag tta gca gac gag     384
Ser Thr Asp Phe Arg Trp His Ile Ile Arg His Lys Leu Ala Asp Glu
        115                 120                 125
```

```
gag acc ttc atg aac gcg gcc aag gcc aga gtt agg cag atg ttg cgc    432
Glu Thr Phe Met Asn Ala Ala Lys Ala Arg Val Arg Gln Met Leu Arg
        130                 135                 140 cct gct gta ggc cca tct att att caa gag ttg gtt cat ctt tgg aat    480
Pro Ala Val Gly Pro Ser Ile Ile Gln Glu Leu Val His Leu Trp Asn
145                 150                 155                 160 gag cct cgg ctg agg ccc ata ctg aaa gag atc gac gga tat cga tat    528
Glu Pro Arg Leu Arg Pro Ile Leu Lys Glu Ile Asp Gly Tyr Arg Tyr
                165                 170                 175 gcc atg tta ttt gct agc cag aac cag atc aca ccc gat atg cta ttg    576
Ala Met Leu Phe Ala Ser Gln Asn Gln Ile Thr Pro Asp Met Leu Leu
            180                 185                 190 cag ctt gac cca gat atg gag ggt gag ttg att cat gga atc gct cag    624
Gln Leu Asp Pro Asp Met Glu Gly Glu Leu Ile His Gly Ile Ala Gln
        195                 200                 205 gag tat ctc atc cat gcg cgc cgg cag gag cag gaa ttc cct cca gtg    672
Glu Tyr Leu Ile His Ala Arg Arg Gln Glu Gln Glu Phe Pro Pro Val
    210                 215                 220 agc gtg gtc gct ttc gaa gga ttc gaa ggt cca ccg ttc gga atg tgc    720
Ser Val Val Ala Phe Glu Gly Phe Glu Gly Pro Pro Phe Gly Met Cys
225                 230                 235                 240 tag                                                                723
```

<210> SEQ ID NO 22
<211> LENGTH: 240
<212> TYPE: PRT
<213> ORGANISM: Agrobacterium vitis

<400> SEQUENCE: 22

```
Met Asp Leu Arg Leu Ile Phe Gly Pro Thr Cys Thr Gly Lys Thr Ser
1               5                   10                  15

Thr Ala Ile Arg Leu Ala Gln Gln Thr Gly Leu Pro Val Leu Ser Leu
            20                  25                  30

Asp Arg Val Gln Cys Cys Pro Gln Leu Ser Thr Gly Ser Gly Arg Pro
        35                  40                  45

Thr Val Glu Glu Leu Lys Gly Thr Thr Arg Leu Tyr Leu Glu Asp Arg
    50                  55                  60

Pro Leu Val Lys Gly Ile Ile Ala Ala Lys Gln Ala His Glu Arg Leu
65                  70                  75                  80

Ile Gly Glu Val Tyr Asn Tyr Glu Ala His Gly Gly Leu Ile Leu Glu
                85                  90                  95

Gly Gly Ser Ile Ser Leu Leu Arg Cys Met Ala Gln Ser Ser Tyr Trp
            100                 105                 110

Ser Thr Asp Phe Arg Trp His Ile Ile Arg His Lys Leu Ala Asp Glu
        115                 120                 125

Glu Thr Phe Met Asn Ala Ala Lys Ala Arg Val Arg Gln Met Leu Arg
    130                 135                 140

Pro Ala Val Gly Pro Ser Ile Ile Gln Glu Leu Val His Leu Trp Asn
145                 150                 155                 160

Glu Pro Arg Leu Arg Pro Ile Leu Lys Glu Ile Asp Gly Tyr Arg Tyr
                165                 170                 175

Ala Met Leu Phe Ala Ser Gln Asn Gln Ile Thr Pro Asp Met Leu Leu
            180                 185                 190

Gln Leu Asp Pro Asp Met Glu Gly Glu Leu Ile His Gly Ile Ala Gln
        195                 200                 205

Glu Tyr Leu Ile His Ala Arg Arg Gln Glu Gln Glu Phe Pro Pro Val
```

-continued

```
                 210                 215                 220
Ser Val Ala Phe Glu Gly Phe Glu Gly Pro Pro Phe Gly Met Cys
225                 230                 235                 240

<210> SEQ ID NO 23
<211> LENGTH: 720
<212> TYPE: DNA
<213> ORGANISM: Dictyostelium discoideum
<220> FEATURE:
<221> NAME/KEY: CDS
<222> LOCATION: (1)..(720)
<223> OTHER INFORMATION:

<400> SEQUENCE: 23 atg gca aca aaa tca aat gaa gag aat att gca gaa ttt aaa ggt cat    48
Met Ala Thr Lys Ser Asn Glu Glu Asn Ile Ala Glu Phe Lys Gly His
1               5                   10                  15 aat gaa att caa att gaa tta atg aaa gaa gaa tgt att gta gtt gat    96
Asn Glu Ile Gln Ile Glu Leu Met Lys Glu Glu Cys Ile Val Val Asp
                20                  25                  30 aat gat gat aaa cca att aga cca gga tca aag aaa gaa act cat tta   144
Asn Asp Asp Lys Pro Ile Arg Pro Gly Ser Lys Lys Glu Thr His Leu
            35                  40                  45 atg gtt aat att aat aat ggc tta ctt cat cgt gca ttc agt att ttc   192
Met Val Asn Ile Asn Asn Gly Leu Leu His Arg Ala Phe Ser Ile Phe
        50                  55                  60 tta ttc aat ggt gaa ggt aaa tta tta ctt caa caa aga gca tta gag   240
Leu Phe Asn Gly Glu Gly Lys Leu Leu Leu Gln Gln Arg Ala Leu Glu
65                  70                  75                  80 aaa atc act ttc cca ggc tat tgg aca aac act gtt tgt tct cat cca   288
Lys Ile Thr Phe Pro Gly Tyr Trp Thr Asn Thr Val Cys Ser His Pro
                85                  90                  95 ctt tgg att gtt ggt tct gaa tta gtt gaa gag aat gct caa ggt gtt   336
Leu Trp Ile Val Gly Ser Glu Leu Val Glu Glu Asn Ala Gln Gly Val
            100                 105                 110 aaa ata gct gca aaa aga aaa tta aat cat gaa tta ggt gta cca tta   384
Lys Ile Ala Ala Lys Arg Lys Leu Asn His Glu Leu Gly Val Pro Leu
        115                 120                 125 gat caa gtc aat atc gat gat ttc act ttt atg act aaa att cat tac   432
Asp Gln Val Asn Ile Asp Asp Phe Thr Phe Met Thr Lys Ile His Tyr
    130                 135                 140 aaa tct gaa tca aaa gaa gat cca caa tgg ggt gaa cat gaa att gat   480
Lys Ser Glu Ser Lys Glu Asp Pro Gln Trp Gly Glu His Glu Ile Asp
145                 150                 155                 160 cat att tta att atg caa aaa gat ggt att aca att aat gct gaa cca   528
His Ile Leu Ile Met Gln Lys Asp Gly Ile Thr Ile Asn Ala Glu Pro
                165                 170                 175 aat gaa gtt atg gac tat aaa tat gta tca caa gaa gaa tta gat caa   576
Asn Glu Val Met Asp Tyr Lys Tyr Val Ser Gln Glu Glu Leu Asp Gln
            180                 185                 190 tta ttt aaa gat gaa gat gaa ggt aaa gtt aaa gta aca cct tgg ttt   624
Leu Phe Lys Asp Glu Asp Glu Gly Lys Val Lys Val Thr Pro Trp Phe
        195                 200                 205 aga tta att gca tta aat cat tta aaa cca tgg tgg aat aat tta aat   672
Arg Leu Ile Ala Leu Asn His Leu Lys Pro Trp Trp Asn Asn Leu Asn
    210                 215                 220 aat tta aaa cca tta gtt gaa cca aca aat aca att cat aga tat taa   720
Asn Leu Lys Pro Leu Val Glu Pro Thr Asn Thr Ile His Arg Tyr
225                 230                 235

<210> SEQ ID NO 24
```

-continued

```
<211> LENGTH: 239
<212> TYPE: PRT
<213> ORGANISM: Dictyostelium discoideum

<400> SEQUENCE: 24

Met Ala Thr Lys Ser Asn Glu Glu Asn Ile Ala Glu Phe Lys Gly His
1               5                   10                  15

Asn Glu Ile Gln Ile Glu Leu Met Lys Glu Glu Cys Ile Val Val Asp
            20                  25                  30

Asn Asp Asp Lys Pro Ile Arg Pro Gly Ser Lys Lys Glu Thr His Leu
        35                  40                  45

Met Val Asn Ile Asn Asn Gly Leu Leu His Arg Ala Phe Ser Ile Phe
    50                  55                  60

Leu Phe Asn Gly Glu Gly Lys Leu Leu Leu Gln Gln Arg Ala Leu Glu
65                  70                  75                  80

Lys Ile Thr Phe Pro Gly Tyr Trp Thr Asn Thr Val Cys Ser His Pro
                85                  90                  95

Leu Trp Ile Val Gly Ser Glu Leu Val Glu Glu Asn Ala Gln Gly Val
            100                 105                 110

Lys Ile Ala Ala Lys Arg Lys Leu Asn His Glu Leu Gly Val Pro Leu
        115                 120                 125

Asp Gln Val Asn Ile Asp Asp Phe Thr Phe Met Thr Lys Ile His Tyr
    130                 135                 140

Lys Ser Glu Ser Lys Glu Asp Pro Gln Trp Gly Glu His Glu Ile Asp
145                 150                 155                 160

His Ile Leu Ile Met Gln Lys Asp Gly Ile Thr Ile Asn Ala Glu Pro
                165                 170                 175

Asn Glu Val Met Asp Tyr Lys Tyr Val Ser Gln Glu Glu Leu Asp Gln
            180                 185                 190

Leu Phe Lys Asp Glu Asp Glu Gly Lys Val Lys Val Thr Pro Trp Phe
        195                 200                 205

Arg Leu Ile Ala Leu Asn His Leu Lys Pro Trp Trp Asn Asn Leu Asn
    210                 215                 220

Asn Leu Lys Pro Leu Val Glu Pro Thr Asn Thr Ile His Arg Tyr
225                 230                 235
```